(12) United States Patent
Keidar

(10) Patent No.: US 10,010,417 B2
(45) Date of Patent: Jul. 3, 2018

(54) LOW-PROFILE PROSTHETIC HEART VALVE FOR REPLACING A MITRAL VALVE

(71) Applicant: Edwards Lifesciences Corporation, Irvine, CA (US)

(72) Inventor: Yaron Keidar, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 89 days.

(21) Appl. No.: 15/130,521

(22) Filed: Apr. 15, 2016

(65) Prior Publication Data
US 2016/0302922 A1  Oct. 20, 2016

Related U.S. Application Data

(60) Provisional application No. 62/148,441, filed on Apr. 16, 2015.

(51) Int. Cl.
*A61F 2/24*  (2006.01)

(52) U.S. Cl.
CPC .......... *A61F 2/2433* (2013.01); *A61F 2/2418* (2013.01); *A61F 2220/0008* (2013.01); *A61F 2250/0063* (2013.01)

(58) Field of Classification Search
CPC ...... A61F 2/2427; A61F 2/243; A61F 2/2433; A61F 2/2436
USPC ...................................................... 623/2.11
See application file for complete search history.

(56) References Cited

U.S. PATENT DOCUMENTS

| | | | |
|---|---|---|---|
| 3,409,013 A | 11/1968 | Berry | |
| 3,472,230 A | 10/1969 | Fogarty | |
| 3,548,417 A | 12/1970 | Kisher | |
| 3,587,115 A | 6/1971 | Shiley | |
| 3,657,744 A | 4/1972 | Ersek | |
| 3,671,979 A | 6/1972 | Moulopoulos | |
| 3,714,671 A | 2/1973 | Edwards et al. | |
| 3,755,823 A | 9/1973 | Hancock | |

(Continued)

FOREIGN PATENT DOCUMENTS

| | | |
|---|---|---|
| DE | 2246526 A1 | 3/1973 |
| DE | 19532846 A1 | 3/1997 |

(Continued)

OTHER PUBLICATIONS

Int'l. Search Report issued for PCT/US2016/026515, dated Jul. 18, 2016.

(Continued)

*Primary Examiner* — Melanie Tyson
(74) *Attorney, Agent, or Firm* — Klarquist Sparkman LLP

(57) ABSTRACT

In one representative embodiment, a prosthetic valve assembly comprises a valve component comprising a radially compressible and expandable frame and a valve structure supported inside of the frame. The valve structure is configured to allow blood to flow through the valve component in one direction and block the flow of blood in the opposite direction. The assembly further comprises a radially compressible and expandable anchor comprising an annular base and a plurality of cantilevered fixation members extending from the base. The fixation members are configured to pivot inwardly toward the valve component when the valve component is radially expanded within the anchor.

20 Claims, 15 Drawing Sheets

(56) References Cited

U.S. PATENT DOCUMENTS

| | | |
|---|---|---|
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Amey |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely et al. |
| 6,575,959 B1 | 6/2003 | Sarge et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin, Jr. et al. |
| 7,018,406 B2 | 3/2006 | Seguin et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,892,281 B2 | 2/2011 | Seguin et al. |
| 7,914,575 B2 | 3/2011 | Guyenot et al. |
| 7,993,394 B2 | 8/2011 | Hariton et al. |
| 8,007,992 B2 | 8/2011 | Tian et al. |

(56) References Cited

U.S. PATENT DOCUMENTS

| | | |
|---|---|---|
| 8,029,556 B2 | 10/2011 | Rowe |
| 8,092,521 B2 | 1/2012 | Figulla et al. |
| 8,118,866 B2 | 2/2012 | Herrmann et al. |
| 8,167,932 B2 | 5/2012 | Bourang |
| 8,206,437 B2 | 6/2012 | Bonhoeffer et al. |
| 8,216,174 B2 | 7/2012 | Wilk et al. |
| 8,317,858 B2 | 11/2012 | Straubinger et al. |
| 8,398,704 B2 | 3/2013 | Straubinger et al. |
| 8,416,643 B2 | 4/2013 | Magee |
| 8,449,599 B2 | 5/2013 | Chau et al. |
| 8,460,370 B2 | 6/2013 | Zakay |
| 9,532,868 B2 | 1/2017 | Braido |
| 9,662,203 B2 | 5/2017 | Sheahan et al. |
| 2001/0021872 A1 | 9/2001 | Bailey et al. |
| 2002/0032481 A1 | 3/2002 | Gabbay |
| 2002/0173842 A1 | 11/2002 | Buchanan |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0039436 A1 | 2/2004 | Spenser et al. |
| 2004/0092858 A1 | 5/2004 | Wilson et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0137688 A1 | 6/2005 | Salahieh et al. |
| 2005/0137698 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2005/0288766 A1 | 12/2005 | Plain et al. |
| 2006/0025857 A1 | 2/2006 | Bergheim et al. |
| 2006/0058872 A1 | 3/2006 | Salahieh et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0195134 A1 | 8/2006 | Crittenden |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2007/0005131 A1 | 1/2007 | Taylor |
| 2007/0010877 A1 | 1/2007 | Salahieh et al. |
| 2007/0027534 A1 | 2/2007 | Bergeim et al. |
| 2007/0066863 A1 | 3/2007 | Rafiee et al. |
| 2007/0088431 A1 | 4/2007 | Bourang et al. |
| 2007/0100439 A1 | 5/2007 | Cangialosi et al. |
| 2007/0112422 A1 | 5/2007 | Dehdashtian |
| 2007/0142906 A1 | 6/2007 | Figulla et al. |
| 2007/0156224 A1 | 7/2007 | Cioanta et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0270943 A1 | 11/2007 | Solem |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0042208 A1 | 2/2010 | Herrmann et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0288634 A1 | 11/2011 | Tuval et al. |
| 2011/0319989 A1 | 12/2011 | Lane et al. |
| 2012/0035722 A1 | 2/2012 | Tuval |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0283823 A1 | 11/2012 | Bonhoeffer et al. |
| 2012/0296418 A1 | 11/2012 | Bonyuet et al. |
| 2012/0310336 A1 | 12/2012 | Figulla et al. |
| 2013/0073035 A1 | 3/2013 | Tuval et al. |
| 2013/0079869 A1 | 3/2013 | Straubinger et al. |
| 2013/0190862 A1 | 7/2013 | Pintor et al. |
| 2013/0197622 A1 | 8/2013 | Mitra et al. |
| 2013/0253635 A1 | 9/2013 | Straubinger et al. |
| 2013/0310928 A1 | 11/2013 | Morriss et al. |
| 2014/0222136 A1* | 8/2014 | Geist .................... A61F 2/2466 623/2.11 |
| 2014/0343665 A1 | 11/2014 | Straubinger et al. |
| 2014/0343669 A1 | 11/2014 | Lane et al. |
| 2014/0364944 A1 | 12/2014 | Lutter et al. |
| 2014/0379074 A1* | 12/2014 | Spence ................ A61F 2/2418 623/2.11 |
| 2015/0216657 A1 | 8/2015 | Braido |
| 2015/0216658 A1 | 8/2015 | Braido |
| 2015/0359631 A1 | 12/2015 | Sheahan et al. |
| 2016/0113764 A1 | 4/2016 | Sheahan et al. |
| 2016/0113766 A1* | 4/2016 | Ganesan ............... A61F 2/2427 623/2.11 |
| 2016/0302922 A1 | 10/2016 | Keidar |
| 2017/0042671 A1 | 2/2017 | Backus et al. |
| 2017/0143485 A1 | 5/2017 | Gorman, III et al. |
| 2017/0209264 A1 | 7/2017 | Chau et al. |
| 2017/0216026 A1 | 8/2017 | Quill et al. |
| 2017/0224484 A1 | 8/2017 | Pintor et al. |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |

(56) References Cited

FOREIGN PATENT DOCUMENTS

| | | |
|---|---|---|
| DE | 10010074 A1 | 10/2001 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 102006052564 B3 | 12/2007 |
| EP | 0103546 A1 | 3/1984 |
| EP | 0144167 A2 | 6/1985 |
| EP | 0592410 A1 | 4/1994 |
| EP | 0597967 A1 | 5/1994 |
| EP | 0850607 A1 | 7/1998 |
| EP | 1057460 A1 | 12/2000 |
| EP | 1088529 A2 | 4/2001 |
| EP | 1469797 A1 | 10/2004 |
| EP | 1570809 A1 | 9/2005 |
| EP | 1653888 A2 | 5/2006 |
| EP | 2777617 A1 | 9/2014 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 91/17720 A1 | 11/1991 |
| WO | 92/17118 A1 | 10/1992 |
| WO | 93001768 A1 | 2/1993 |
| WO | 97/24080 A1 | 7/1997 |
| WO | 98/29057 A1 | 7/1998 |
| WO | 99/33414 A1 | 7/1999 |
| WO | 99/40964 A1 | 8/1999 |
| WO | 99/47075 A1 | 9/1999 |
| WO | 00/18333 A1 | 4/2000 |
| WO | 00/41652 A1 | 7/2000 |
| WO | 00/47139 A1 | 8/2000 |
| WO | 0128459 A1 | 4/2001 |
| WO | 01/35878 A2 | 5/2001 |
| WO | 01/49213 A2 | 7/2001 |
| WO | 01/62189 A1 | 8/2001 |
| WO | 0154624 A1 | 8/2001 |
| WO | 0154625 A1 | 8/2001 |
| WO | 01/64137 A1 | 9/2001 |
| WO | 01/76510 A2 | 10/2001 |
| WO | 02/22054 A1 | 3/2002 |
| WO | 02/36048 A1 | 5/2002 |
| WO | 02/41789 A2 | 5/2002 |
| WO | 02/43620 A1 | 6/2002 |
| WO | 02/47575 A2 | 6/2002 |
| WO | 02/49540 A2 | 6/2002 |
| WO | 03/047468 A1 | 6/2003 |
| WO | 05/034812 | 4/2005 |
| WO | 05/087140 A1 | 9/2005 |
| WO | 05/102015 | 11/2005 |
| WO | 06/014233 A2 | 2/2006 |
| WO | 06/034008 A2 | 3/2006 |
| WO | 06/108090 | 10/2006 |
| WO | 06/111391 | 10/2006 |
| WO | 06/138173 | 12/2006 |
| WO | 08/005405 A2 | 1/2008 |
| WO | 08/035337 A2 | 3/2008 |
| WO | 08/147964 A1 | 3/2008 |
| WO | 08/150529 A1 | 12/2008 |
| WO | 09/024859 | 2/2009 |
| WO | 09/116041 | 9/2009 |

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Al Zaibag, Muayed, et al., "Percutaneous Balloon Valvotomy in Tricuspid Stenosis," British Heart Journal, Jan. 1987, vol. 57, No. 1, pp. 51-53.

Andersen, et al., "Transluminal implantation of artificial heart valves. Description of a new expandable aortic valve and initial results with implantation by catheter technique in closed chest pigs." European Heart Journal (1992), 13, 704-708.

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Dake, Transluminal Placement of Endovascular Stent-Grafts for the Treatment of Descending Thoracic Aortic Aneurysms, New Engl. J.Med., 1994; 331:1729 34.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., M.D., David D., "Percutaneous Endovascular Graft: Experimental Evaluation," Radiology 1897; 163: 357-360.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

Rashkind, M.D., William J., "Creation of an Atrial Septal Defect Withoput Thoracotomy," the Journal of the American Medical Association, vol. 196, No. 11, Jun. 13, 1966, pp. 173-174.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida, Barry T., et al., "Modifications of Gianturco Expandable Wire Stents," AJR:150, May 1988, Dec. 3, 1987, pp. 1185-1187.

Urban, M.D., Philip, "Coronary Artery Stenting," Editions Médecine et Hygiène, Genève, 1991, pp. 5-47.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Wheatley, M.D., David J., "Valve Prostheses," Rob & Smith's Operative Surgery, Fourth Edition, pp. 415-424, Butterworths 1986.

* cited by examiner

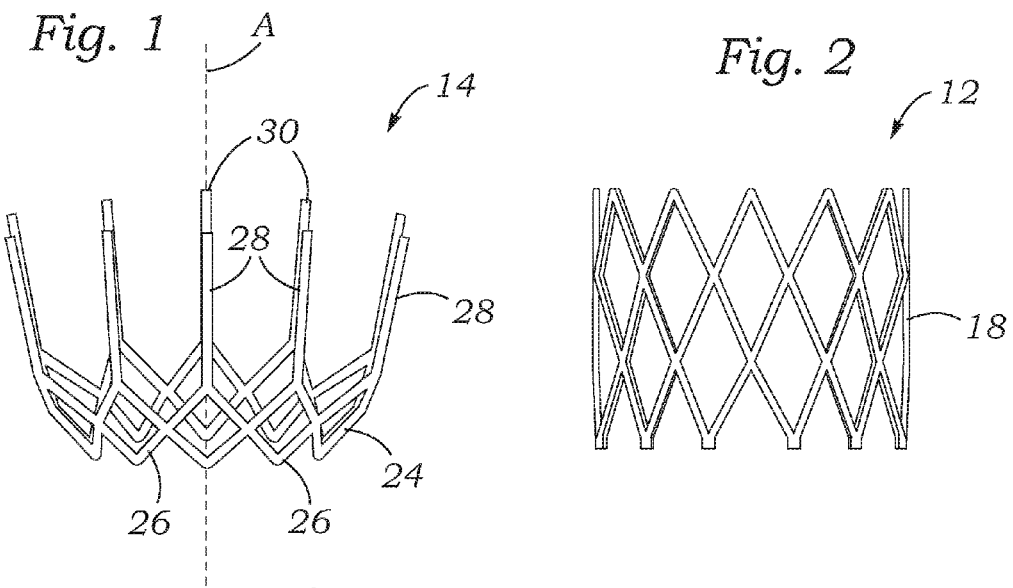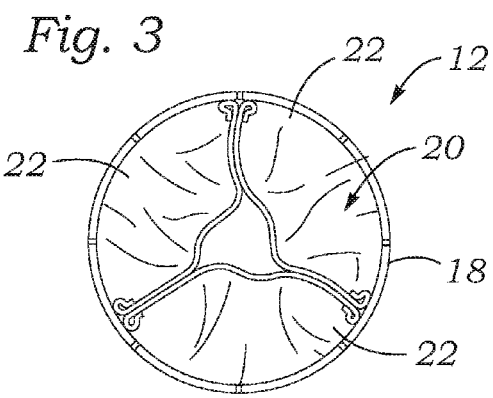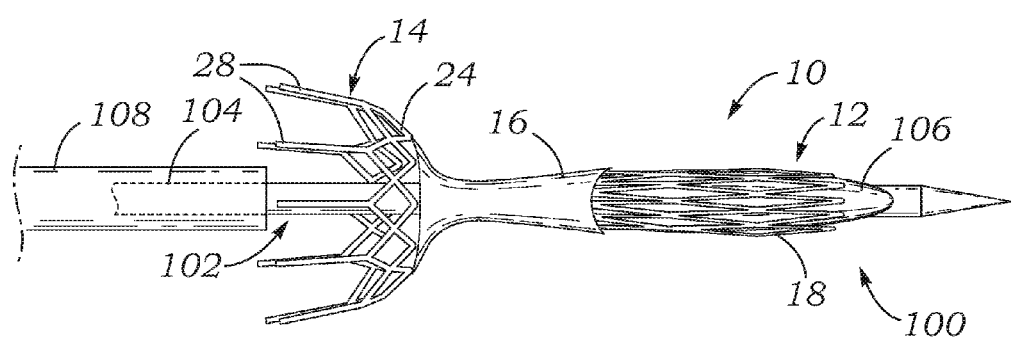

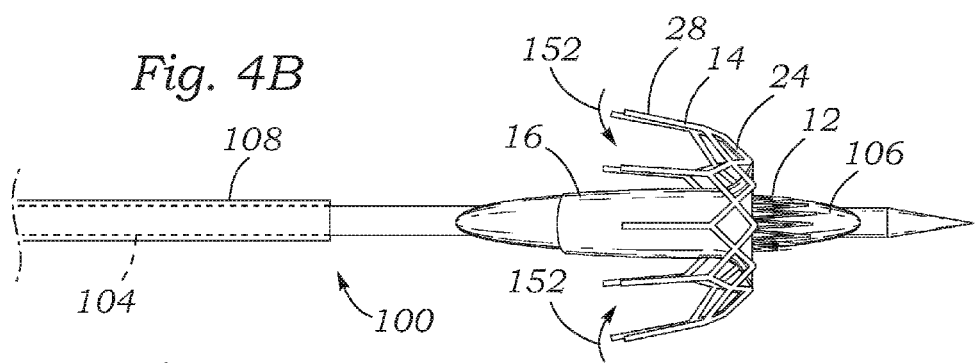
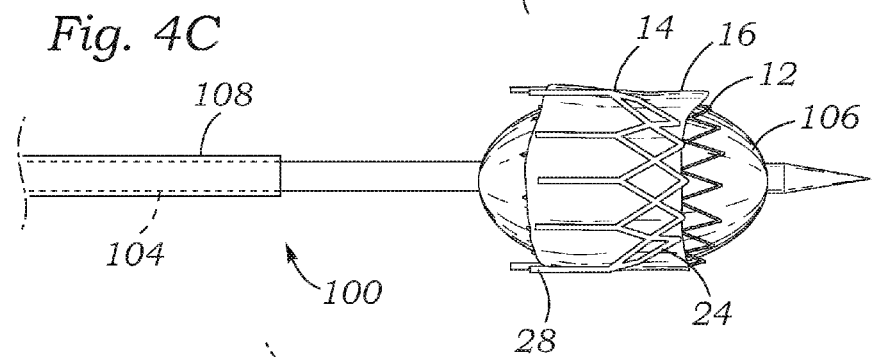
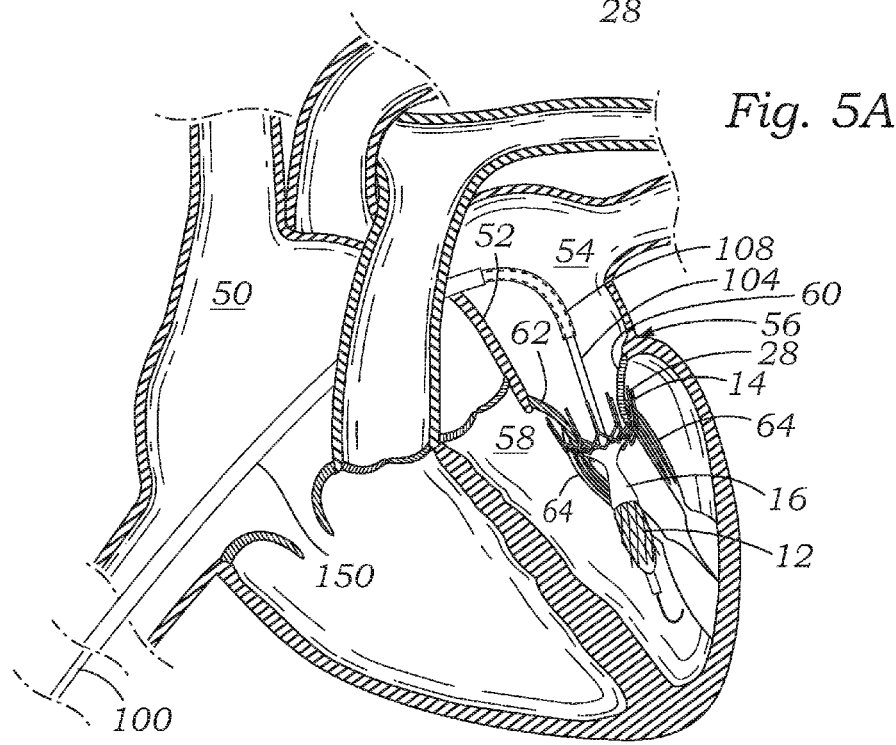

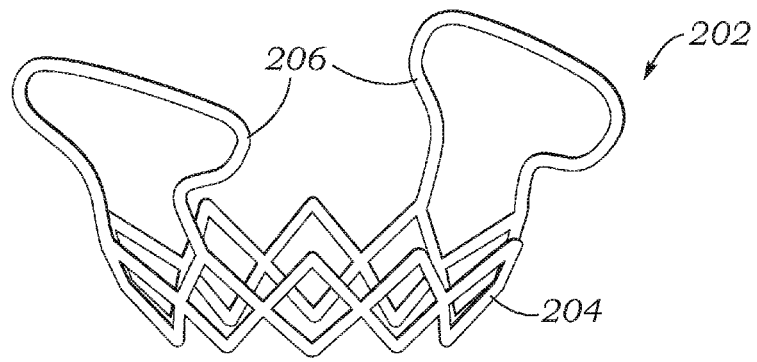
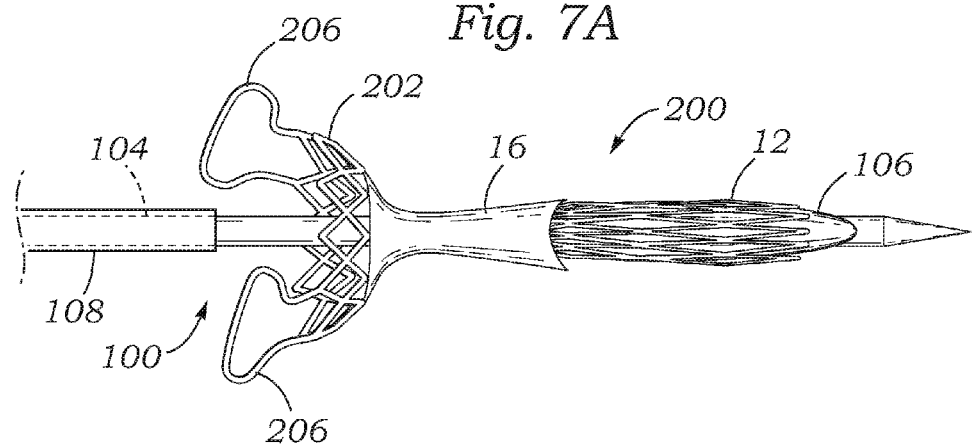
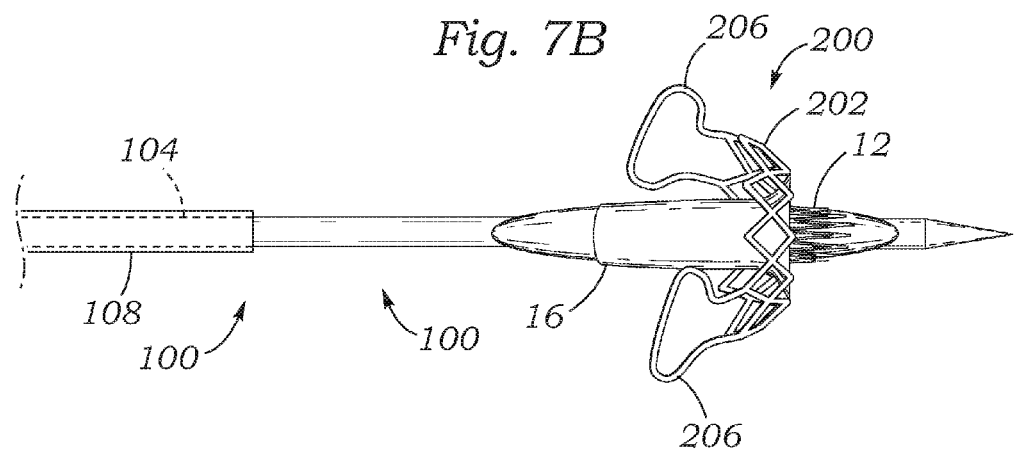

LOW-PROFILE PROSTHETIC HEART VALVE FOR REPLACING A MITRAL VALVE

CROSS-REFERENCE TO RELATED APPLICATION

The present application claims the benefit of U.S. Provisional Application No. 62/148,441, filed Apr. 16, 2015, which is incorporated herein by reference.

FIELD

This disclosure pertains generally to prosthetic devices for repairing and/or replacing native heart valves, and in particular to prosthetic valves for replacing defective mitral valves, as well as methods and devices for delivering and implanting the same within a human heart.

BACKGROUND

Prosthetic valves have been used for many years to treat cardiac valvular disorders. The native heart valves (i.e., the aortic, pulmonary, tricuspid, and mitral valves) serve many critical functions in assuring the forward flow of an adequate supply of blood through the cardiovascular system. These heart valves can be rendered less effective by congenital malformations, inflammatory processes, infectious conditions, or disease. Such damage to the valves can result in serious cardiovascular compromise or death. For many years the definitive treatment for such disorders was the surgical repair or replacement of the valve during open-heart surgery. Such surgeries are highly invasive and are prone to many complications, however. Therefore, elderly and frail patients with defective heart valves often go untreated. More recently a transvascular technique has been developed for introducing and implanting a prosthetic heart valve using a flexible catheter in a manner that is much less invasive than open-heart surgery.

In this technique, a prosthetic valve is mounted in a crimped state on the end portion of a flexible catheter and advanced through a blood vessel of the patient until the prosthetic valve reaches the implantation site. The prosthetic valve at the catheter tip is then expanded to its functional size at the site of the defective native valve, such as by inflating a balloon on which the prosthetic valve is mounted.

Another known technique for implanting a prosthetic aortic valve is a transapical approach where a small incision is made in the chest wall of a patient and the catheter is advanced through the apex (i.e., bottom tip) of the heart. Like the transvascular approach, the transapical approach can include a balloon catheter having a steering mechanism for delivering a balloon-expandable prosthetic heart valve through an introducer to the aortic annulus. The balloon catheter can include a deflectable segment just proximal to the distal balloon to facilitate positioning of the prosthetic heart valve in the proper orientation within the aortic annulus.

The above techniques and others have provided numerous options for high operative risk patients with aortic valve disease to avoid the consequences of open heart surgery and cardiopulmonary bypass. While devices and procedures for the aortic valve are well-developed, such catheter-based procedures are not necessarily applicable to the mitral valve due to the distinct differences between the aortic and mitral valve.

For example, compared to the aortic valve, which has a relatively round and firm annulus (especially in the case of aortic stenosis), the mitral valve annulus can be relatively less firm and more unstable. Consequently, it may not be possible to secure a prosthetic valve that is designed primarily for the aortic valve within the native mitral valve annulus by relying solely on friction from the radial force of an outer surface of a prosthetic valve pressed against the native mitral annulus. Also, the mitral valve has a complex subvalvular apparatus, e.g., the chordae tendineae and papillary muscles, which is not present in the aortic valve and which can make placement of a prosthetic valve difficult.

Known prosthetic valves for the mitral valve typically include anchoring devices on the outside of an annular frame to assist in anchoring the prosthetic valve to surrounding tissue. Such anchoring devices can limit the ability to crimp the prosthetic valve, which can increase the overall crimp profile of the prosthetic valve. Prior art anchoring devices also tend to increase the rigidity of the prosthetic valve in the crimped state, which can limit the ability to flex/steer the delivery catheter within the patient's vasculature. Moreover, prior art anchoring devices also can be difficult to position at their desired anchoring locations due to the presence of the subvalvular tissue.

Thus, a need exists for transcatheter prosthetic mitral valves that overcome one or more of these disadvantages of the prior art.

SUMMARY

In one representative embodiment, a prosthetic valve assembly comprises a valve component comprising a radially compressible and expandable frame and a valve structure supported inside of the frame. The valve structure is configured to allow blood to flow through the valve component in one direction and block the flow of blood in the opposite direction. The assembly further comprises a radially compressible and expandable anchor comprising an annular base and a plurality of cantilevered fixation members extending from the base. The fixation members are configured to pivot inwardly toward the valve component when the valve component is radially expanded within the anchor.

In some embodiments, the valve assembly further comprises a flexible sleeve having a first end secured to the frame of the valve component and a second end secured to the anchor. The sleeve is configured to allow the valve component and the anchor to move between a delivery configuration in which the valve component and the anchor are axially spaced from each other and an operating configuration in which the valve component is positioned co-axially within the anchor.

In some embodiments, the fixation members extend radially outwardly and circumferentially relative to a longitudinal axis of the anchor.

In another representative embodiment, a prosthetic mitral valve assembly for replacing a native mitral valve comprises a valve component comprising a radially compressible and expandable frame and a valve structure supported inside of the frame. The valve structure is configured to allow blood to flow through the valve component in one direction and block the flow of blood in the opposite direction. The assembly further comprises a radially compressible and expandable anchor comprising an annular base and a plurality of cantilevered ventricular fixation members extending from the base, wherein the fixation members are configured to extend radially outside of the native mitral valve leaflets when implanted at the native mitral valve. The assembly can also comprise a flexible connector having a first end portion secured to the frame of the valve component and a second end portion secured to the anchor. The connector is configured to allow the valve component and the anchor to move between a delivery configuration in which the valve component and the anchor are axially spaced from each other and an operating configuration in which the valve component is positioned co-axially within the anchor. The connector has first and second surfaces and is invertable when the valve component is moved from the delivery configuration to the operating configuration such that the first surface is an inner surface and the second surface is an outer surface when the valve component is in the delivery configuration, and the first surface is an outer surface and the second surface is an inner surface when the valve component is in the operating configuration.

In another representative embodiment, a method comprises introducing a delivery apparatus into a patient's body, wherein a prosthetic valve assembly is mounted on a distal end portion of the delivery apparatus; advancing the prosthetic valve assembly into the left ventricle of the heart of the patient; radially expanding an anchor of the prosthetic valve assembly; positioning fixation members of the anchor behind the native mitral valve leaflets and/or the chordae tendineae; and radially expanding a valve component within the anchor, which causes the fixation members to pivot inwardly against the native mitral valve leaflets, thereby clamping the native mitral valve leaflets between the anchor and the valve component.

The foregoing and other objects, features, and advantages of the invention will become more apparent from the following detailed description, which proceeds with reference to the accompanying figures.

BRIEF DESCRIPTION OF THE DRAWINGS

FIG. 1 is a perspective view of an anchor for a prosthetic valve assembly, according to one embodiment.

FIG. 2 is a side elevation view of a stent for a valve component of a prosthetic valve assembly, according to one embodiment.

FIG. 3 is a top plan view of a valve component of a prosthetic valve assembly, according to one embodiment.

FIGS. 4A-4C are enlarged side views of a prosthetic valve assembly incorporating the anchor of FIG. 1 shown mounted on a delivery apparatus at various stages of deployment, according to one embodiment.

FIGS. 5A-5D show an exemplary method for delivering and implanting the prosthetic valve assembly of FIGS. 4A-4C at the native mitral valve of the heart.

FIG. 6 is a perspective view of another embodiment of an anchor for a prosthetic valve assembly.

FIGS. 7A-7C are enlarged side views of a prosthetic valve assembly incorporating the anchor of FIG. 6 shown mounted on a delivery apparatus at various stages of deployment, according to one embodiment.

DETAILED DESCRIPTION

General Considerations

Figure 5B:
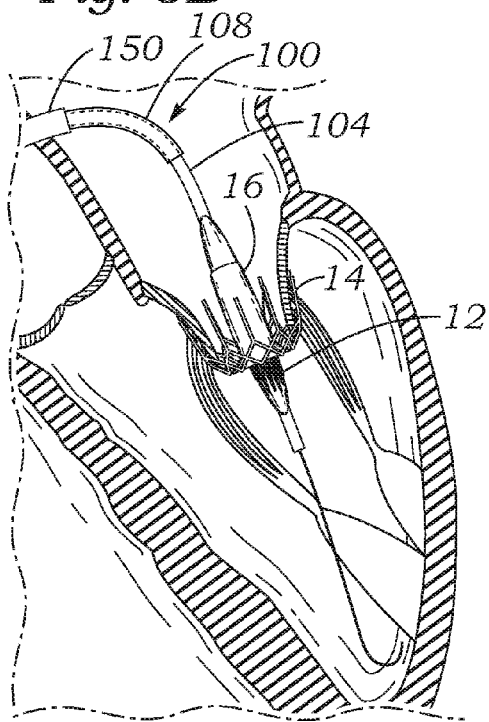

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and sub-combinations with one another. The methods, devices, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C."

As used herein, the term "coupled" generally means physically coupled or linked and does not exclude the presence of intermediate elements between the coupled items absent specific contrary language.

The terms "delivery configuration" and "operating configuration" refer to the arrangement of the components of the replacement valve assembly relative to one another, and each term includes both crimped and non-crimped (e.g., expanded) states.

Terms such as "above," "upper," "below," and "lower" are meant only to show the position of some features relative to others as shown in the drawings, and do not necessarily correlate to actual positions or directions of those features when the replacement valve is being delivered and/or is in its implanted configuration or position.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Moreover, for the sake of simplicity, the figures may not show the various ways (readily discernable, based on this disclosure, by one of ordinary skill in the art) in which the disclosed system, method, and apparatus can be used in combination with other systems, methods, and apparatuses.

Overview

Described herein are embodiments of prosthetic valves and components thereof that are primarily intended to be implanted at the mitral valve region of a human heart, as well as devices and methods for implanting the same. The prosthetic valves can be used to help restore and/or replace the functionality of a defective native valve. These prosthetic valves are not restricted to use at the native mitral valve annulus, however, and can be used to replace other valves within the heart, such as the tricuspid valve, aortic valve, and pulmonary valve. In some cases, the disclosed devices can also be used to replace a venous valve or generate a valved or valveless fistula or patent foramen ovale (PFO).

Disclosed embodiments of a prosthetic heart valve can be designed for delivery and implantation using minimally invasive techniques. For example, disclosed replacement heart valves can be crimped onto a delivery catheter, navigated through a patient's vasculature, and expanded before or during implantation in a native valve site, such as the native mitral valve. As such, the minimum crimped diameter (e.g., the profile of the crimped replacement valve on the delivery system) can be of utmost importance to the success and/or ease of performing of the procedure.

Disclosed embodiments of a prosthetic heart valve have anchoring structure that is configured to permit anchoring of the prosthetic valve at the mitral position yet does not contribute to the overall crimp profile.

Referring first to FIG. 4A, there is shown a prosthetic valve assembly 10 mounted on a delivery apparatus 100, according to one embodiment. The prosthetic valve assembly 10 in the illustrated embodiment comprises a valve component 12, an outer anchor 14, and a flexible sleeve or connecting portion that is secured at opposite ends to the valve component 12 and the anchor 14. The valve assembly 10 is configured to transform or move between a delivery configuration in which the valve component 12 and the anchor 14 are spaced apart from each other for transcatheter delivery into and through a patient's body (FIG. 4A) and a deployed or operating (functional) configuration in which the valve component is placed co-axially within the anchor and both components are radially expanded (FIG. 4C). The anchor 14 is configured to anchor the valve component to the native heart valve and/or surrounding tissue, as further described below.

As best shown in FIGS. 2-3, the valve component 12 comprises a stent or frame 18 and a valve structure 20 comprising one or more leaflets 22 supported by the frame. The frame 18 can have a wire mesh-like configuration and can be radially collapsible and expandable between a radially expanded state and a radially compressed state to enable delivery and implantation at an atrioventricular valve region of the heart (i.e., at the mitral or tricuspid valve region). The wire mesh can include metal wires or struts arranged in a lattice pattern, such as a sawtooth or zig-zag pattern, but other patterns may also be used. The frame 18 can comprise a shape-memory material, such as Nitinol, to enable self-expansion from the radially compressed state to the expanded state. In other embodiments, the frame 18 can be plastically expandable from a radially compressed state to an expanded state by an expansion device, such as an inflatable balloon, for example. Such plastically expanding frames can comprise stainless steel, chromium alloys, and/or other suitable materials.

The leaflets 22 can comprise any of various suitable materials, such as natural tissue (e.g., bovine pericardial tissue) or synthetic materials. The leaflets 22 can be mounted to the frame 18 using suitable techniques and mechanisms (e.g., sutures). In some embodiments, leaflets 22 can be sutured to the frame 18 in a tricuspid arrangement, as shown in FIG. 3.

The valve component 12 can also include a blood-impermeable skirt or sealing member mounted on the outside and/or the inside of the frame 18. The skirt can be connected to the inner and/or outer surfaces of the frame 18 to form at least one layer or envelope covering some or all of the openings in the frame. The skirt can be connected to the frame 18, for example, by sutures. The skirt can comprise a fabric that is impermeable to blood but can allow for tissue ingrowth. The skirt can comprise synthetic materials, such as polyester material or a biocompatible polymer. One example of a polyester material is polyethylene terephthalate (PET). Another example is expanded polytetrafluoroethylene (ePTFE), either alone, or in combination at least one other material. Alternative materials can also be used. For example, the skirt can comprise biological matter, such as pericardial tissue (e.g., bovine, porcine, or equine pericardium) or other biological tissue.

Additional details regarding components and assembly of prosthetic valves (including techniques for mounting leaflets to the frame) are described, for example, in U.S. Patent Application Publication No. 2009/0276040 A1, U.S. Patent Publication No. 2010/0217382 A1, U.S. Patent Publication No. 2012/0123529 A1, and U.S. Patent Publication No. 2012/0239142 A1, which are incorporated by reference herein.

As best shown in FIG. 1, the outer anchor 14 comprises an annular ring or base 24 at a lower end of the anchor. The ring 24 can be comprised of a plurality of struts 26 arranged in a lattice configuration that allows the anchor to be radially collapsible and expandable between a radially expanded state and a radially compressed state to enable delivery and implantation at an atrioventricular valve region of the heart. Extending from the ring 24 are a plurality of circumferentially spaced, cantilevered fixation members, prongs, or arms, 28. The arms 28 in the illustrated embodiment extend radially outwardly from a longitudinally axis A of the anchor 14 such that the anchor generally has an overall conical shape that flares extending in a direction from the ring 24 toward the opposite end of the anchor.

The anchor 14 can comprise a shape-memory material, such as Nitinol, to enable self-expansion from the radially compressed state to the expanded state. In other embodiments, the anchor 14 can be plastically expandable from a radially compressed state to an expanded state by an expansion device, such as an inflatable balloon, for example.

The sleeve 16 can comprise any suitable flexible and/or elastic biocompatible material, such as any of various synthetic fabrics (e.g., PET fabric) or natural tissue (e.g., bovine pericardial tissue). In particular embodiments, the sleeve 16 is non-porous or substantially non-porous to blood and can serve as an outer skirt or sealing member that minimizes or prevents paravalvular leakage along the outside of the valve component 12.

In particular embodiments, the frame 18 of the valve component 12 comprises a plastically-expandable material and the anchor 14 comprises a shape-memory material. The delivery apparatus 100, shown in FIG. 4A, is one example of a delivery apparatus for delivering and deploying an assembly 10 comprising a plastically-expandable frame 18 and a self-expandable anchor 14. As shown, the delivery apparatus 100 can comprise a balloon catheter 102 comprising an elongated shaft 104 and an inflatable balloon 106 (or equivalent expansion mechanism) mounted on the distal end portion of the shaft 104. The valve component 12 is shown crimped onto the balloon 106 for delivery into a patient's body. The delivery apparatus 100 can also include a delivery sheath 108 that is configured to receive and retain the anchor 14 in a crimped, radially compressed state for delivery into the patient's body.

The proximal end portions of the sheath 108 and the shaft 104 can be connected to a common handle, which can be configured to permit relative longitudinal and/or rotational movement between the shaft 104 and the sheath 108. The handle can also include a locking or latching mechanism that allows a user to selectively lock the longitudinal and/or rotational position of the shaft relative to the sheath or vice versa.

In some cases, for safety and/or other reasons, the disclosed prosthetic devices may be delivered from the atrial side of the atrioventricular valve annulus. Delivery from the atrial side of the native valve annulus can be accomplished in various manners. For example, a transatrial approach can be made through an atrial wall, which can be accessed, for example, by an incision through the chest. Atrial delivery can also be made intravascularly, such as from a pulmonary vein. The prosthetic valve assembly can be delivered to the right atrium via the inferior or superior vena cava. In some cases, left atrial delivery can be made via a trans-septal approach, as described in detail below. In a trans-septal approach, an incision can be made in the atrial portion of the septum to allow access to the left atrium from the right atrium. The prosthetic valve assembly can also be delivered via a transventricular approach (through an incision in the chest and in the wall of the left ventricle), or a transfemoral approach (through the femoral artery and the aorta).

To deliver the prosthetic valve assembly 10 to the native mitral valve annulus, the valve component 12 is crimped onto the balloon 106 and the anchor 14 is loaded into the sheath 108 and retained in a radially compressed state. Delivery and placement of the prosthetic valve assembly can be angularly independent, such that the prosthetic valve assembly does not require any special rotational alignment relative to the longitudinal axis of the prosthetic valve assembly. Thus, during delivery, the prosthetic valve assembly may not require any special rotational placement so as to align the ventricular anchors with particular anatomical landmarks (such as the native valve leaflets, particular portions thereof, native valve commissures, chordae tendineae, and/or location of the aortic valve).

FIGS. 4A-4C and 5A-5D show an exemplary process for delivering the prosthetic valve assembly 10 via a trans-septal approach. As show in FIG. 5A, a delivery assembly can include an outer catheter 150, which can be advanced into the right atrium 50 (such as via the inferior vena cava) and then used to create a puncture through the intra-atrial septum 52. The outer catheter 150 can be advanced through the septum until a distal end portion of the outer catheter extends into the left atrium 54.

The delivery apparatus 100 (with the valve component 12 crimped onto the balloon 106 and the anchor 14 within the sheath 108) can be advanced through the outer catheter 150 and into the left ventricle 54. The delivery apparatus 100 can have a steering mechanism that allows the user to adjust the curvature of the distal end portion of the delivery apparatus such that the distal end portion can be directed toward the native mitral valve 56, as shown in FIG. 5A. The steering mechanism can comprise, for example, one or more pull wires having distal ends fixed at a location along the distal end portion of the delivery apparatus and proximal ends operatively coupled to an adjustment knob on the handle. Further details of a steering mechanism and other components of a delivery apparatus that can be implemented in the delivery apparatus 100 are disclosed in U.S. Publication No. 2012/0239142 A1.

After adjusting the curvature of the distal end portion of the delivery apparatus 100, the delivery apparatus can be advanced through the native mitral valve 56 until the entire valve assembly 10 is positioned in the left ventricle 58. The sheath 108 can then be retracted in the proximal direction to allow the anchor 14 to self-expand to its radially expanded, functional shape. FIGS. 4A and 5A show the anchor 14 in the expanded, shape-set state after retraction of the sheath 108. As shown in FIG. 5A, the delivery apparatus 100 can then be retracted proximally to positioned the arms 28 of the anchor 14 behind the native mitral valve leaflets 60, 62. Positioning of the anchor 14 behind the native leaflets also can allow the arms 28 to extend through and engage portions of the native chordae tendineae 64. In this position, the ring 24 of the anchor 14 desirably is just below the free ends of the native leaflets 60, 62.

Referring next to FIGS. 4B and 5B, the delivery apparatus 100 is further retracted proximally to pull the valve component 12 within the native leaflets 60, 62 and co-axially within the anchor 14. Retracting the valve component 14 also causes the sleeve 16 to become inverted and extend over the valve component 12.

Figure 5C:
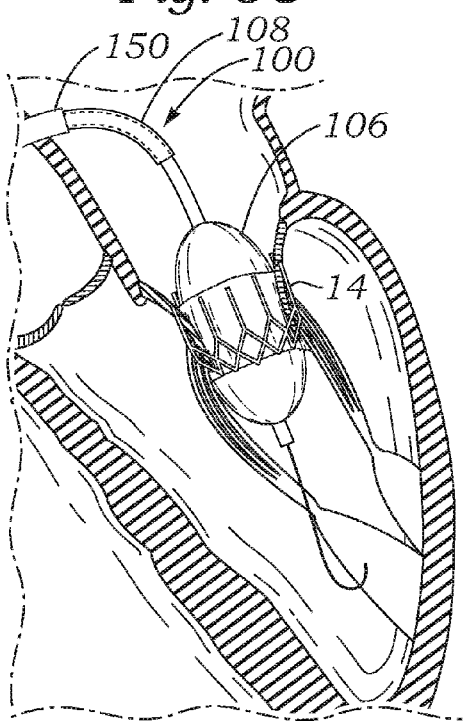

Referring next to FIGS. 4C and 5C, the balloon 106 can be inflated, causing the valve component 12 to radially expand to its functional size. During expansion of the valve component 12, the valve component exerts a force in the radial direction against the ring 24, which in turn causes the arms 28 of the anchor 14 to pivot radially inwardly against the native leaflets 60, 62, as indicated by arrows 152 in FIG. 4B. The arms 28 pinch or compress the native leaflets between the valve component 12 and the anchor 14, thereby anchoring the valve assembly in place within the native mitral valve 56. The inverted sleeve 16 provides an atraumatic landing zone for the valve component 12, shielding the valve component from direct contact with the free ends 30 of the arms 28 during subsequent expansion of the valve component.

Figure 5D:
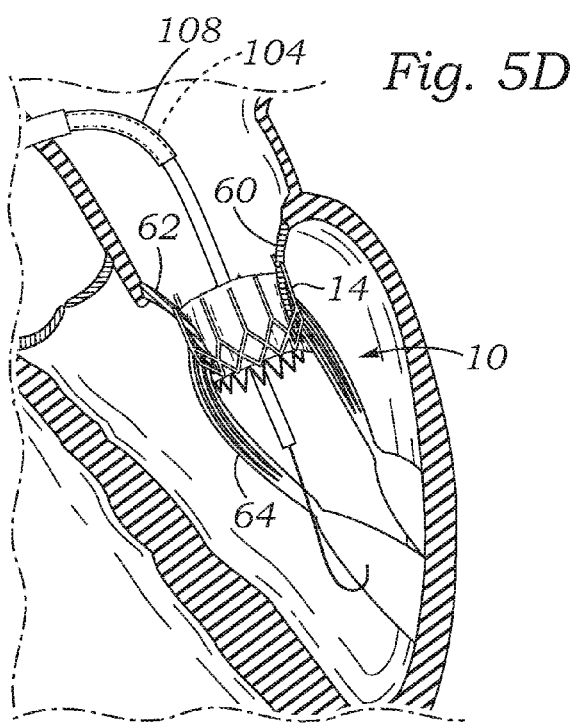

Following deployment of the valve component 12, the balloon 106 can be deflated, and the delivery apparatus 100 and the outer catheter 150 can be removed from the body, as shown in FIG. 5D.

Advantageously, the anchor 14 and the valve component 12 are axially spaced from each other prior to insertion into the patient's body. As such, the anchor and the valve component can be easily crimped and can achieve a relatively small crimped profile that facilitates insertion and delivery through the patient's vasculature.

Figure 7C:
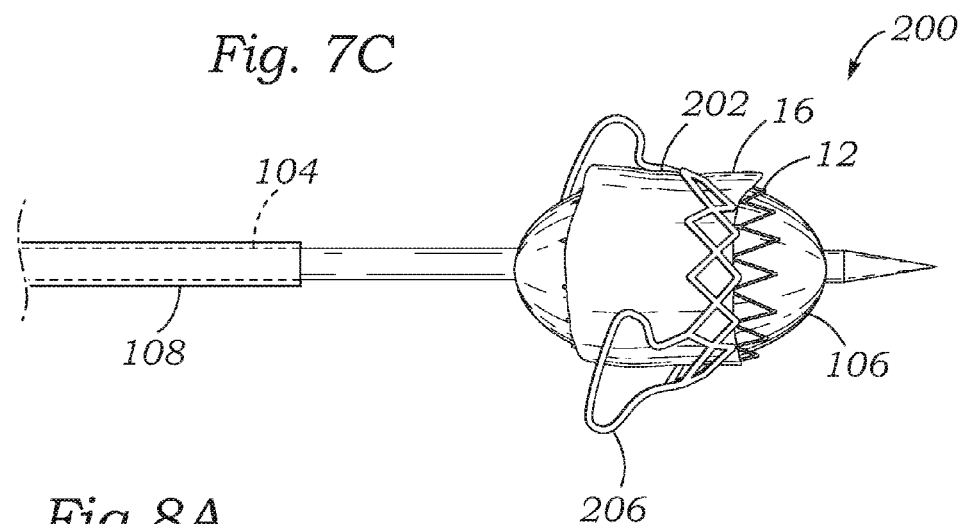

FIGS. 6 and 7A show a prosthetic valve assembly 200, according to another embodiment, comprising a valve component 12, an outer anchor 202, and a flexible sleeve or connecting portion 16 that is secured at opposite ends to the valve component 12 and the anchor 202. The valve assembly 200 can be identical to the valve assembly 10, except that the anchor 14 of FIG. 1 is replaced with the anchor 202. Thus, components that are common to the valve assembly 10 and the valve assembly 200 are given the same respective reference numbers and are not described further. The anchor 202 comprises an annular base or ring 204 and two or more paddle-shaped arms, or fixation members, 206 extending from the ring 204. In the illustrated embodiment, the anchor 202 comprises two fixation members 206 on diametrically opposed sides of the ring 204, although the spacing and number of fixation members 206 can be varied in other embodiments.

FIGS. 7A-7C and 8A-8D show an exemplary process for delivering and implanting the prosthetic valve assembly 200 via a trans-septal procedure. The steps for delivering and implanting the valve assembly 200 can be accomplished as previously described above in connection with the valve assembly 10. When placing the fixation members 206 behind the native leaflets 60, 62, the fixation members 206 can be positioned at the A2 and P2 positions of the native leaflets such that each fixation member is placed between the chordae tendineae of the respective native leaflet. In other embodiments, the fixation members 206 can be placed behind portions of the chordae tendineae. Upon expansion of the valve component 12, the fixation members 206 pivot inwardly and clamp the native tissue (the native leaflets and/or portions of the chordae tendineae) between the valve component 12 and the anchor 202.

FIGS. 9A-9B and 10A-10B show a prosthetic valve assembly 300, according to another embodiment, comprising a valve component 12, an outer anchor 302, and a flexible sleeve or connecting portion 16 that is secured at opposite ends to the valve component 12 and the anchor 302. The valve assembly 300 can be identical to the valve assembly 10, except that the anchor 14 of FIG. 1 is replaced with the anchor 302. Thus, components that are common to the valve assembly 10 and the valve assembly 300 are given the same respective reference numbers and are not described further.

Figure 9A:
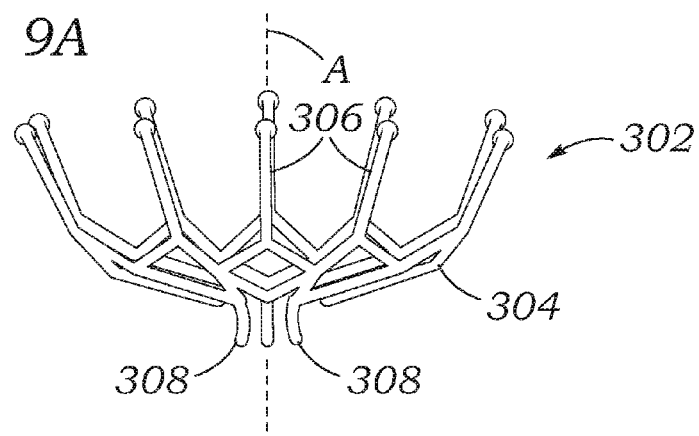
FIG. 9A is a perspective view of another embodiment of an anchor for a prosthetic valve assembly shown in a radially expanded, shape-set state.
Figure 9B:
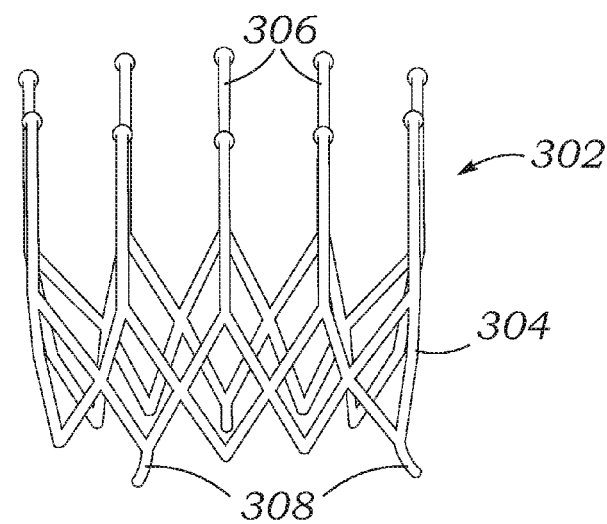
FIG. 9B is a perspective view of the anchor of FIG. 9A shown in a further expanded state by deployment of a valve component within the anchor.

FIG. 9A shows the anchor 302 in a radially expanded, shape-set state after deployment from the delivery sheath 108. FIG. 9B shows the anchor 302 in a further expanded state after the valve component 12 is expanded inside of the anchor 302 (the valve component is omitted in FIG. 9B for purposes of illustration). As shown, the anchor 302 comprises an annular base or ring 304, a plurality of elongated prongs, arms, or fixation members 306 extending from an upper end of the ring 304 (the upper end being the proximal or inflow end of the ring in the illustrated embodiment), and a plurality of prongs, or arms, 308 extending from a lower end of the ring 304 (the lower end being the distal or outflow end of the ring in the illustrated embodiment).

In the radially expanded, shape-set state (FIG. 9A), the fixation members 306 desirably flare or extend radially outwardly from each other and a longitudinal axis A such that the anchor generally has an overall conical shape. The lower prongs 308 desirably curve outwardly away from the lower end of the ring 304. The lower prongs 308 serve as a fulcrum to promote inward pivoting of the fixation members 306 against the native leaflets during deployment. Thus, when the valve component 12 is expanded inside of the anchor 302, the outward radial expansion force against the lower prongs 308 cause the fixation members 306 to pivot inwardly against the native leaflets, which in turn are pressed against the sleeve 16 and the valve component 12 to anchor the valve assembly 300 in place.

Figure 10A:
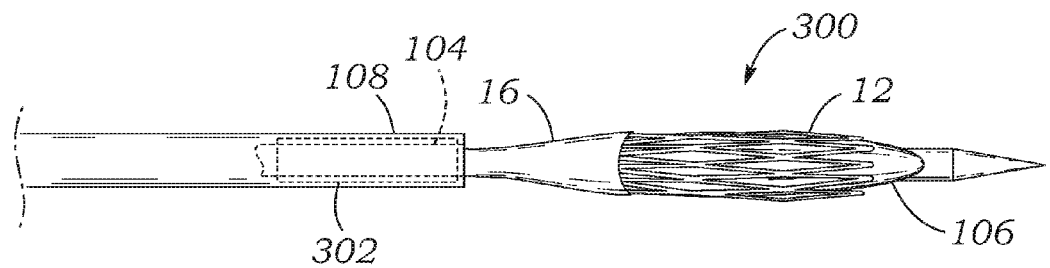
FIGS. 10A-10D are enlarged side views of a prosthetic valve assembly incorporating the anchor of FIGS. 9A-9B shown mounted on a delivery apparatus at various stages of deployment, according to one embodiment.
Figure 10B:
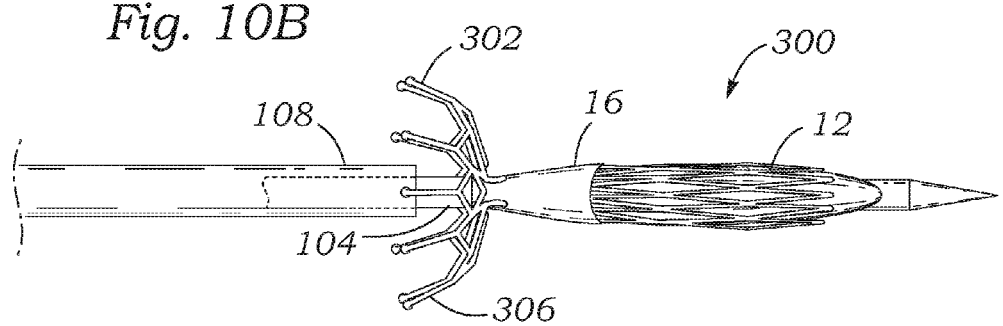
Figure 10C:
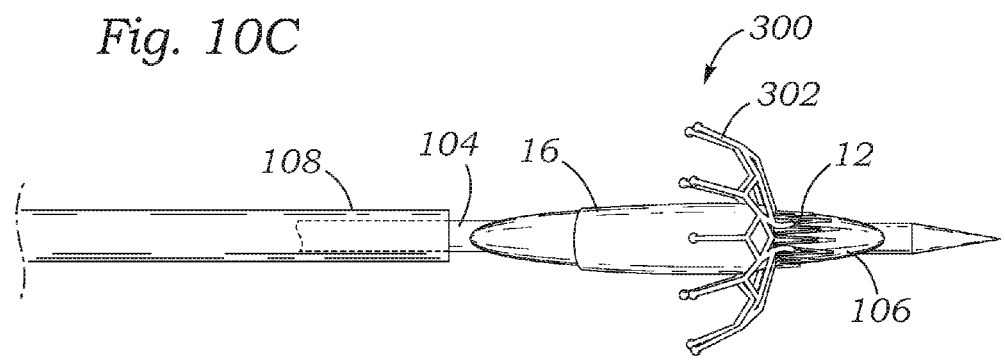
Figure 10D:
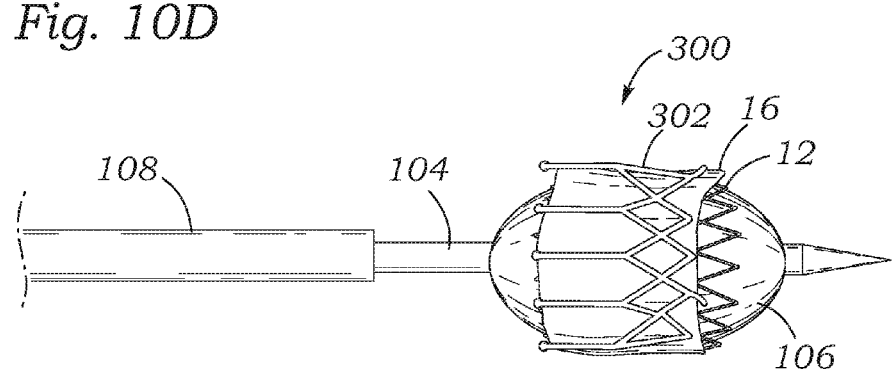
Figure 11A:
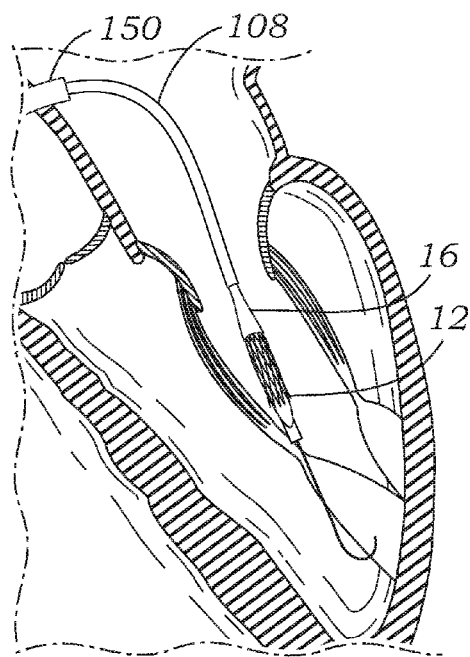
FIGS. 11A-11D show an exemplary method for delivering and implanting the prosthetic valve assembly of FIGS. 10A-10D at the native mitral valve of the heart.
Figure 11B:
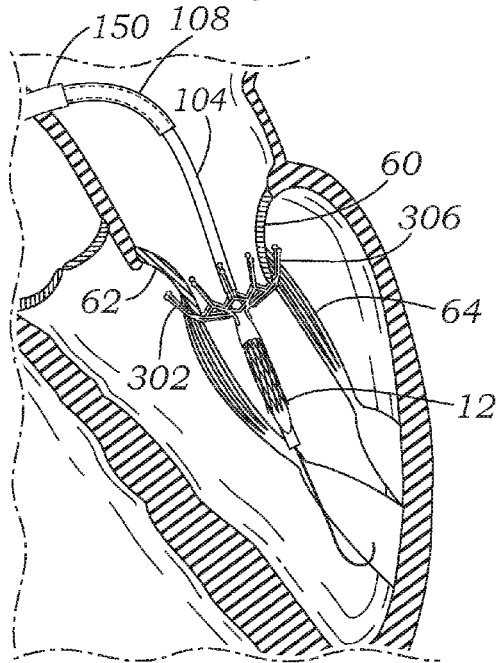
Figure 11C:
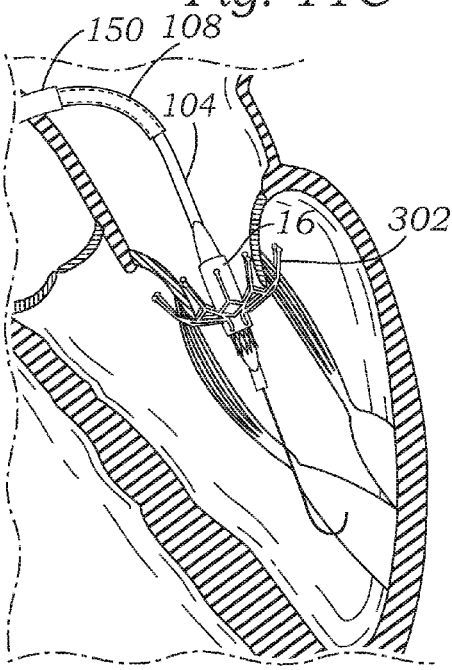
Figure 11D:
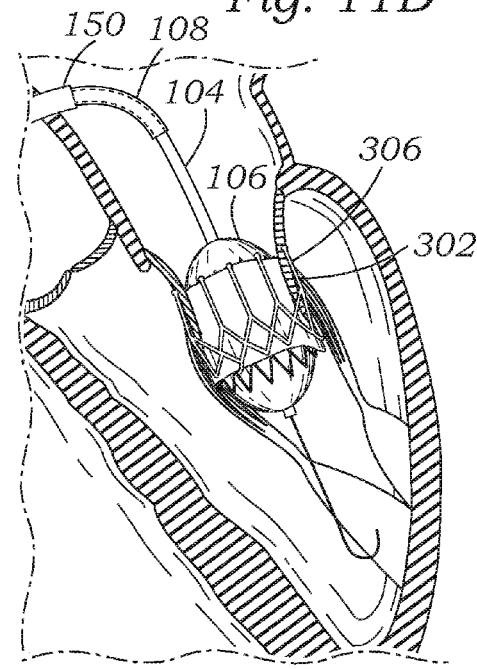

FIGS. 10A-10D and 11A-11D show an exemplary process for delivering and implanting the prosthetic valve assembly 300 via a trans-septal procedure. FIGS. 10A and 11A show the sheath 108 extending over and retaining the anchor 302 in a radially compressed state for delivery into the heart. FIGS. 10B and 11B show the sheath 108 in a retracted position and the anchor 302 in a radially expanded, shape-set state so that the fixation members 306 can be placed behind the native leaflets 60, 62 (FIG. 11B). FIGS. 10C and 11C show the valve component 12 moved inside of the anchor 302 and the native leaflets 60, 62. FIGS. 10D and 11D show the anchor 302 further expanded by inflating the balloon 106, which causes the fixation members 306 to press inwardly against the native leaflets 60, 62 to anchor the valve assembly 300 in place. Additional details regarding the steps for delivering and implanting the valve assembly 300 can be the same as previously described above in connection with the valve assembly 10 and therefore are not repeated here.

FIGS. 12A-12B and 13A-13B show a prosthetic valve assembly 400, according to another embodiment, comprising a valve component 12, an outer anchor 402, and a flexible sleeve or connecting portion 16 that is secured at opposite ends to the valve component 12 and the anchor 402. The valve assembly 400 can be identical to the valve assembly 10, except that the anchor 14 of FIG. 1 is replaced with the anchor 402. Thus, components that are common to the valve assembly 10 and the valve assembly 400 are given the same respective reference numbers and are not described further.

Figure 12A:
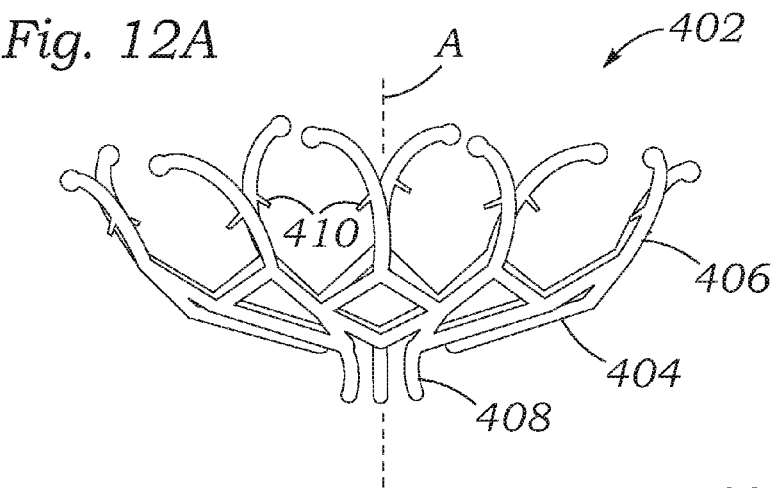
FIG. 12A is a perspective view of another embodiment of an anchor for a prosthetic valve assembly shown in a radially expanded, shape-state.
Figure 12B:
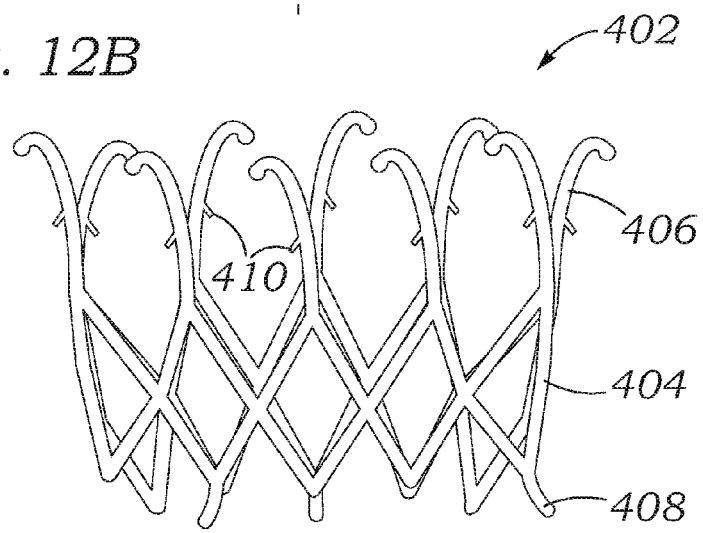
FIG. 12B is a perspective view of the anchor of FIG. 12A shown in a further expanded state by deployment of a valve component within the anchor.

FIG. 12A shows the anchor 402 in a radially expanded, shape-set state after deployment from the delivery sheath 108. FIG. 12B shows the anchor 402 in a further expanded state after the valve component 12 is expanded inside of the anchor 402 (the valve component is omitted in FIG. 12B for purposes of illustration). As shown, the anchor 402 comprises an annular base or ring 404, a plurality of elongated prongs, arms, or fixation members 406 extending from an upper end of the ring 404 (the upper end being the proximal or inflow end of the ring in the illustrated embodiment), and a plurality of prongs, or arms, 408 extending from a lower end of the ring 404 (the lower end being the distal or outflow end of the ring in the illustrated embodiment).

In the radially expanded, shape-set state (FIG. 12A), the fixation members 406 desirably flare or extend radially outwardly from each other and curve circumferentially around a longitudinal axis A. The fixation members 406 can have barbs or hooks 410 located on the inside of the curve defined by the respective fixation member. The fixation members 406 are configured to draw or pull the native leaflets 60, 62 and/or the chordae tendineae 64 inwardly toward the sleeve 16 and the valve component 12, as further described below. The lower prongs 408 desirably curve outwardly away from the lower end of the ring 304.

Figure 13A:
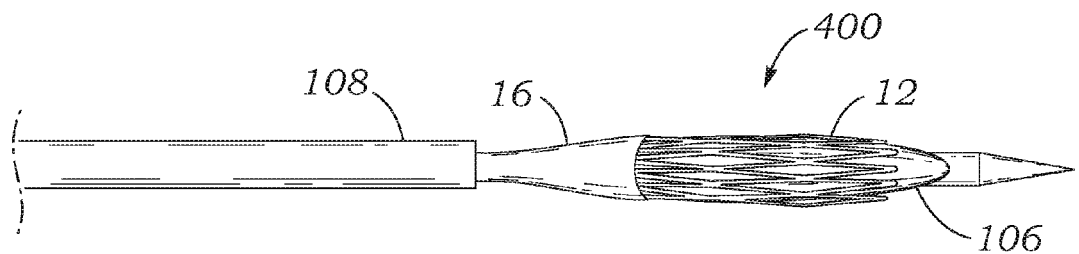
FIGS. 13A-13E are enlarged side views of a prosthetic valve assembly incorporating the anchor of FIGS. 12A-12B shown mounted on a delivery apparatus at various stages of deployment, according to one embodiment.
Figure 13B:
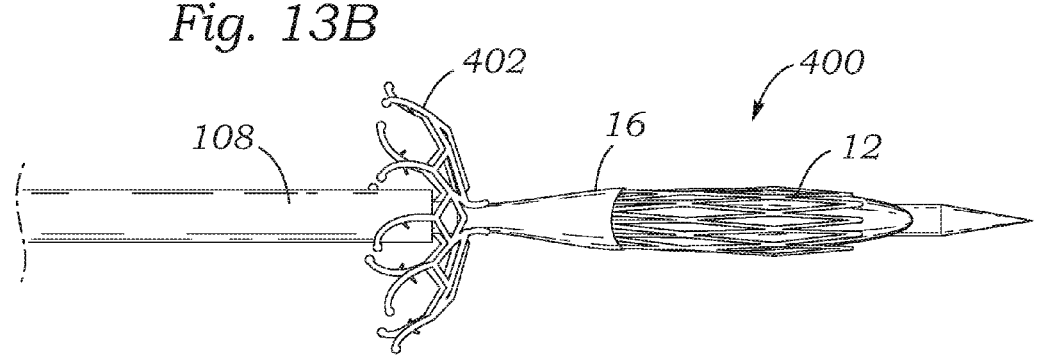
Figure 13C:
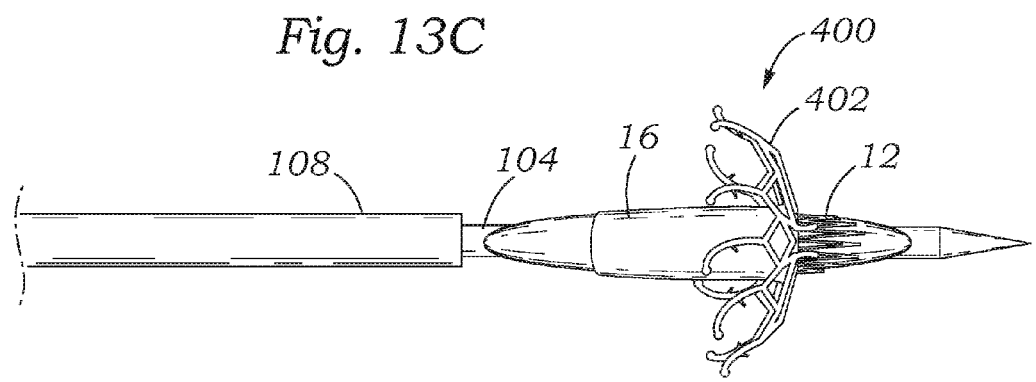
Figure 13D:
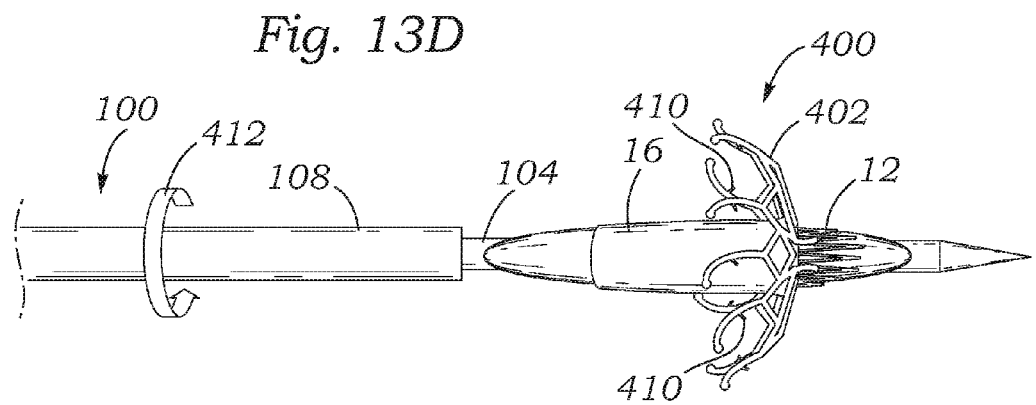
Figure 13E:
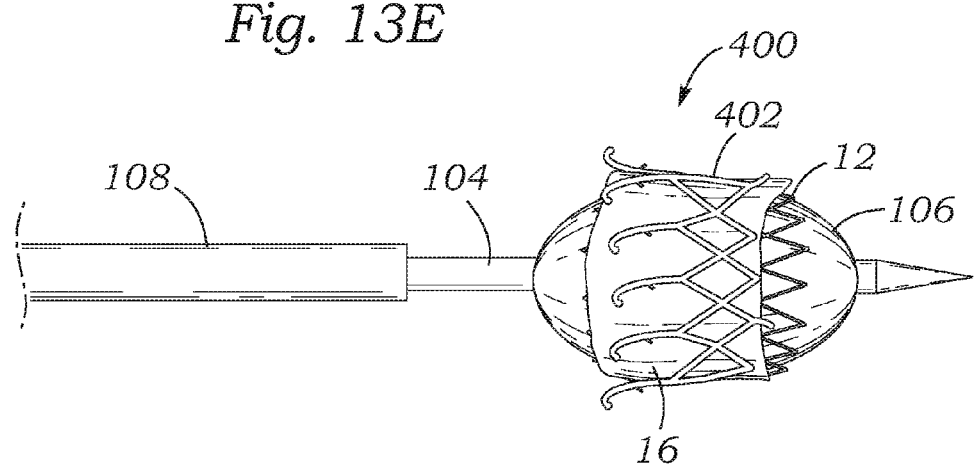
Figure 14A:
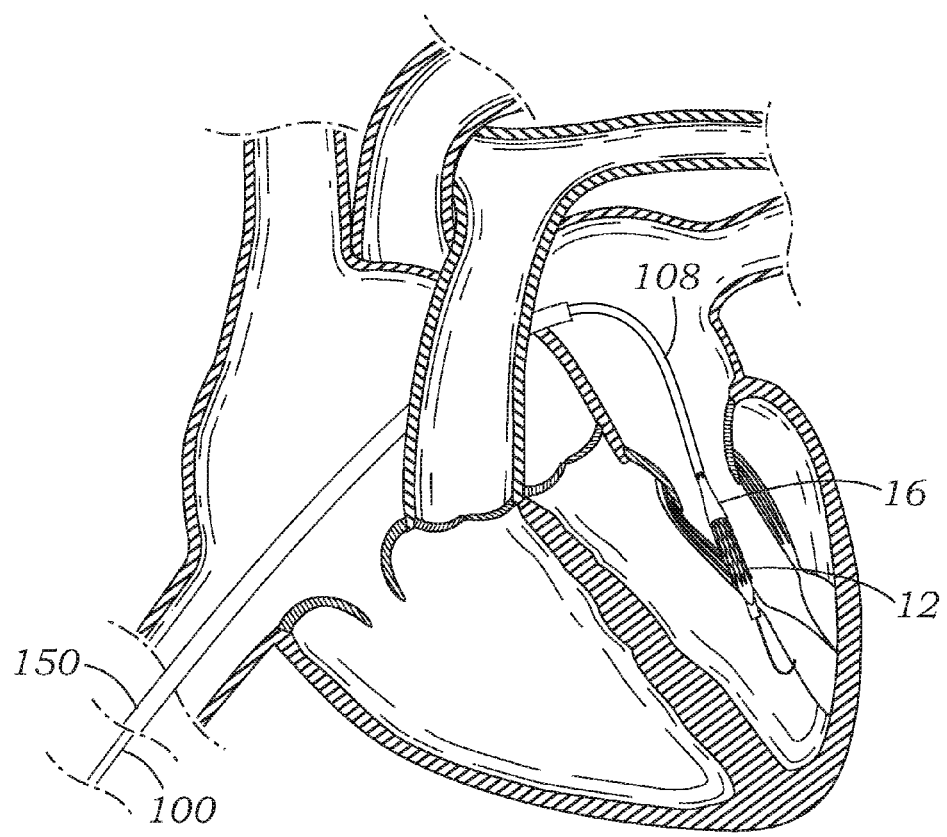
FIGS. 14A-14E show an exemplary method for delivering and implanting the prosthetic valve assembly of FIGS. 13A-13E at the native mitral valve of the heart.
Figure 14B:
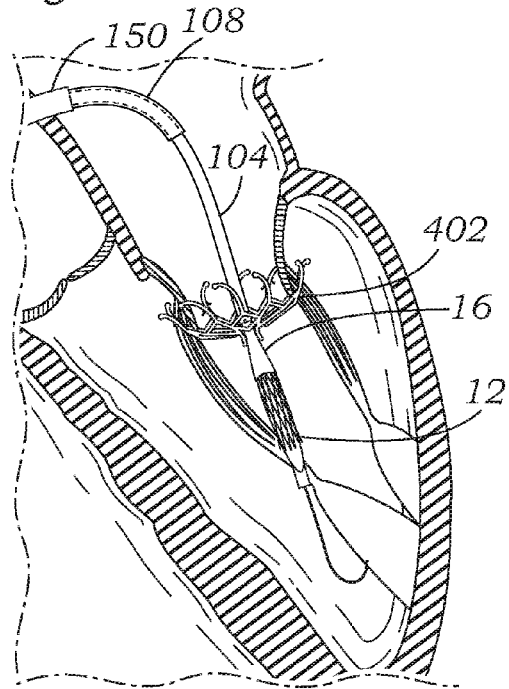
Figure 14C:
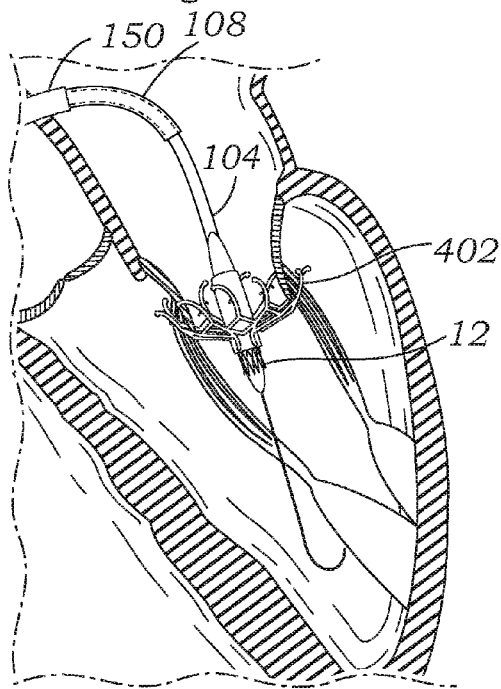

FIGS. 13A-13E and 14A-14E show an exemplary process for delivering and implanting the prosthetic valve assembly 300 via a trans-septal procedure. FIGS. 13A and 14A show the sheath 108 extending over and retaining the anchor 402 in a radially compressed state for delivery into the heart. FIGS. 13B and 14B show the sheath 108 in a retracted position and the anchor 402 in a radially expanded, shape-set state so that the fixation members 406 can be placed behind the native leaflets 60, 62 (FIG. 14B). FIGS. 13C and 14C show the valve component 12 moved inside of the anchor 302 and the native leaflets 60, 62.

Figure 14D:
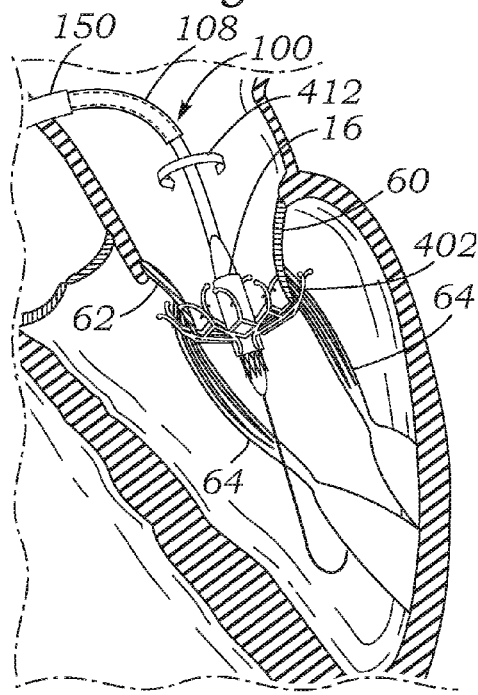

Referring to FIGS. 13D and 14D, the delivery apparatus 100 can be rotated in the direction of arrow 412 to rotate the valve assembly 400 relative to the native tissue. Rotation of the valve assembly 400 causes the fixation members 406 to rotate behind and/or through the chordae tendineae 64. Due to the spiral shape of the fixation members 406, the native leaflets and/or the chordae tendineae are drawn inwardly toward the sleeve 16 and the valve component 12. As the fixation members 406 are rotated, at least some of the chordae tendineae pass over and become lodged behind the hooks 410, which help keep the chordae tendineae tensioned in a partially wound or twisted state around the valve component 12 and prevent unwinding of the chordae tendineae and rotation of the valve assembly in the opposite direction once the valve assembly is released from the delivery apparatus 100.

Figure 14E:
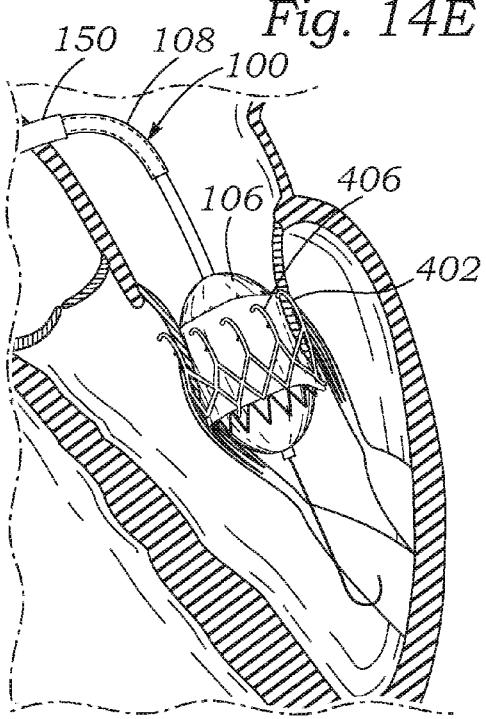

Referring to FIGS. 13E and 14E, after rotating the valve assembly 400, the anchor 402 can be further expanded by inflating the balloon 106, which causes the fixation members 406 to press inwardly against the native leaflets 60, 62. The radial force of the fixation members as well as the engagement of the chordae tendineae through rotation of the fixation members anchors the valve assembly in place within the native mitral valve. The native leaflets 60, 62 are pulled inwardly against the sleeve 16 and/or the valve component 12 through rotation of the fixation members, thereby enhancing the seal of the native tissue against the valve assembly to prevent or minimize paravalvular leakage. Additional details regarding the steps for delivering and implanting the valve assembly 400 can be the same as previously described above in connection with the valve assembly 10 and therefore are not repeated here.

Figure 15:
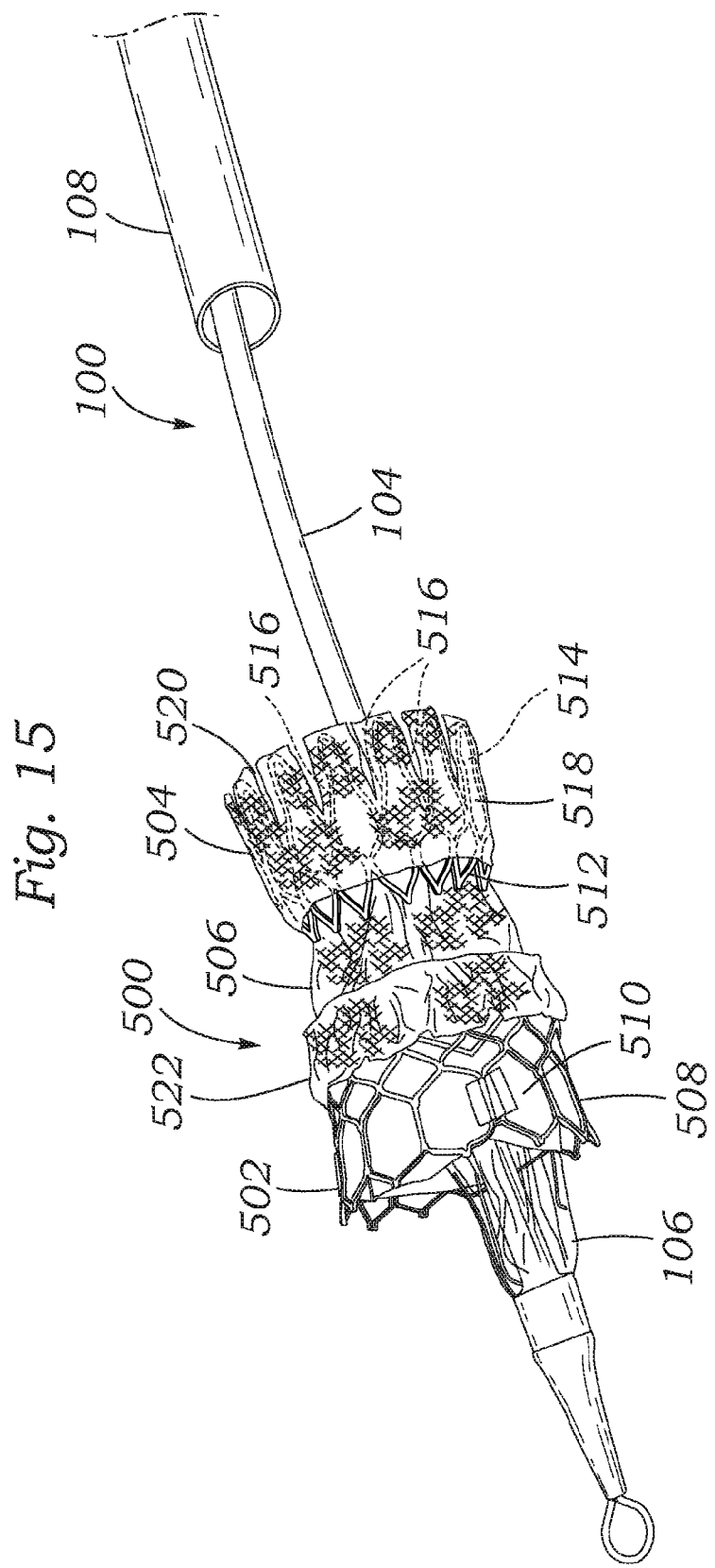
FIG. 15 is a perspective view of another embodiment of a prosthetic valve assembly and a delivery apparatus.

FIG. 15 shows a prosthetic valve assembly 500, according to another embodiment, disposed on a delivery apparatus 100. The prosthetic valve assembly 500 in the illustrated embodiment comprises a valve component 502, an outer anchor 504, and a flexible sleeve or connecting portion 506 that is secured at opposite ends to the valve component 502 and the anchor 504. The valve component 502 comprises an annular frame 508 and a leaflet assembly 510 mounted inside of the frame 508.

The anchor 504 in the illustrated embodiment comprises an annular base or ring 512 comprising a row of diamond shaped cells formed by a plurality of circumferentially extending angled struts. Extending from an outflow end of the ring 512 are a plurality of prongs, arms, or fixation members 514. Each fixation member 514 can comprise two struts 516 that extend from respective cells of the ring 512 and are connected to each other at their ends opposite the ring. The anchor 504 can include an outer skirt 518 (e.g., a fabric skirt) mounted on the outside of the ring 512 and the fixation members 514 to minimize trauma to the native tissue and promote sealing with the valve component 502. Alternatively, the skirt 518 can be on the inside of the anchor or there can be a skirt on the inside and outside of the anchor. As shown, the skirt 518 can have longitudinal slits 520 between the fixation members 514 to allow the fixation members to be placed between the native chordae tendineae.

The sleeve 506 can be connected at one end to the inside of the anchor 504 and at its opposite end to the outside of the frame 508 of the valve component 502. The end of the sleeve 506 that is secured to the frame 508 can form a sealing member on the outside of the frame 508. For example, that end of the sleeve 506 can extend along the outside of the frame 508 and can be folded against itself so as to form an annular sealing member 522 extending around the outside of the frame 508. The sealing member 522 in other words can be formed by an extension portion of the sleeve 506 that includes an inner layer extending along the frame and an outer folded layer. In other embodiments, the sealing member 522 can comprise a single layer of material.

The prosthetic valve assembly 500 can be delivered and implanted in the native mitral valve using the delivery apparatus 100, as previously described.

Figure 8A:
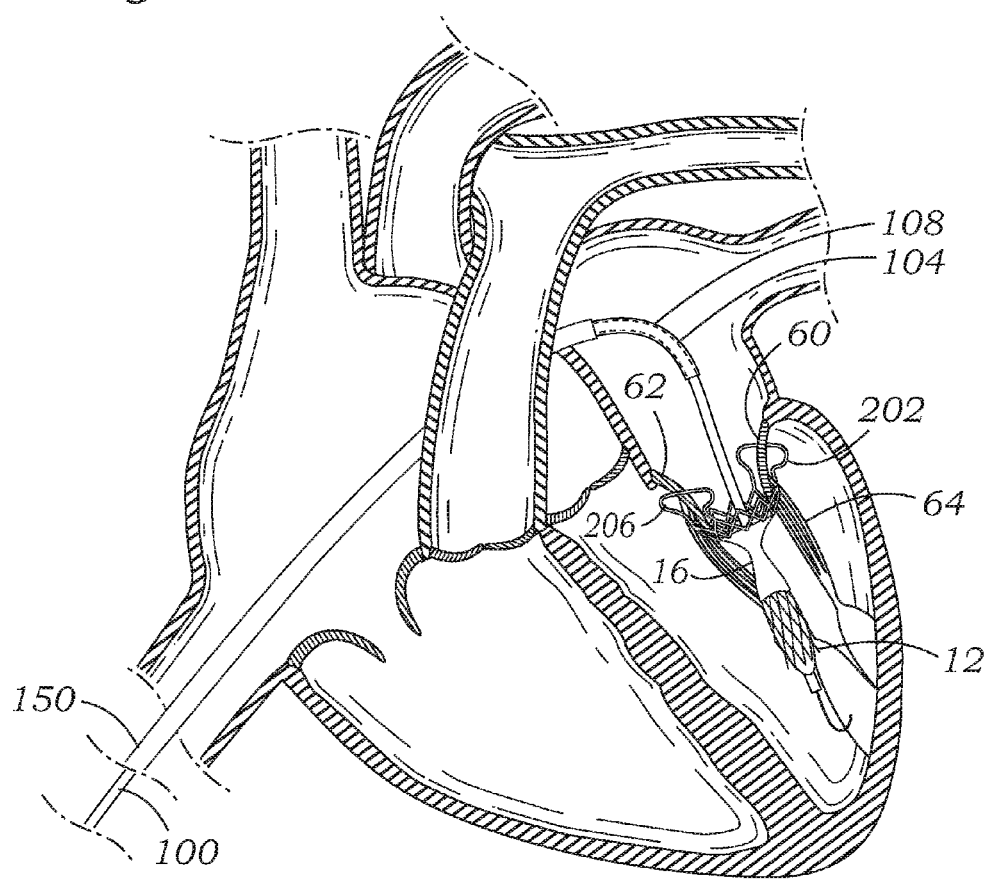
FIGS. 8A-8D show an exemplary method for delivering and implanting the prosthetic valve assembly of FIGS. 7A-7C at the native mitral valve of the heart.
Figure 8B:
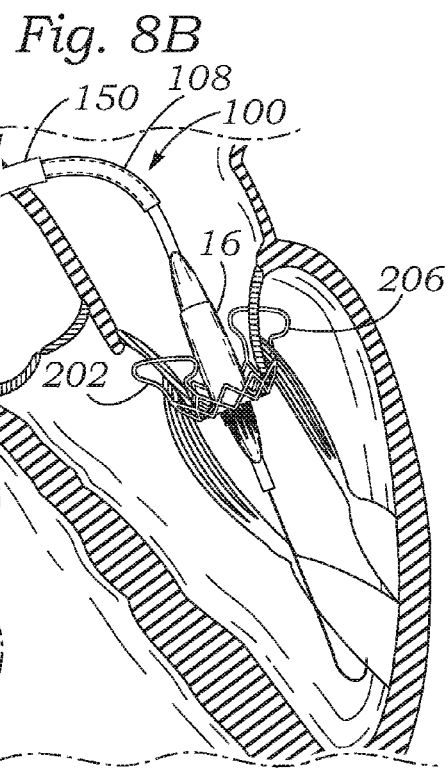
Figure 8C:
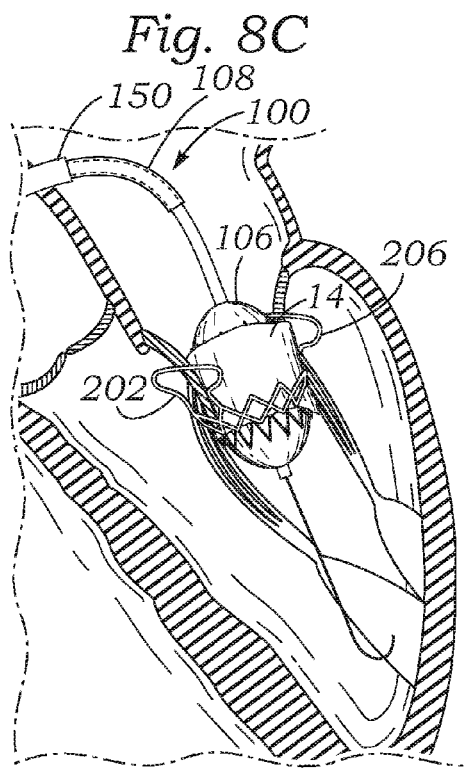
Figure 8D:
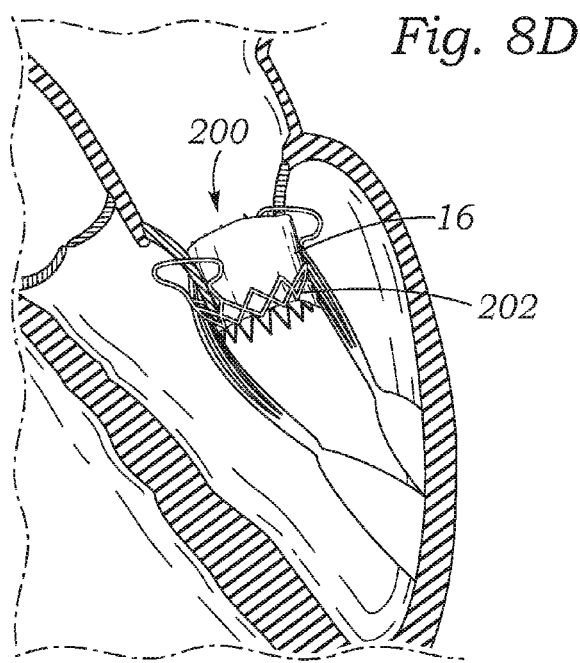
Figure 16:
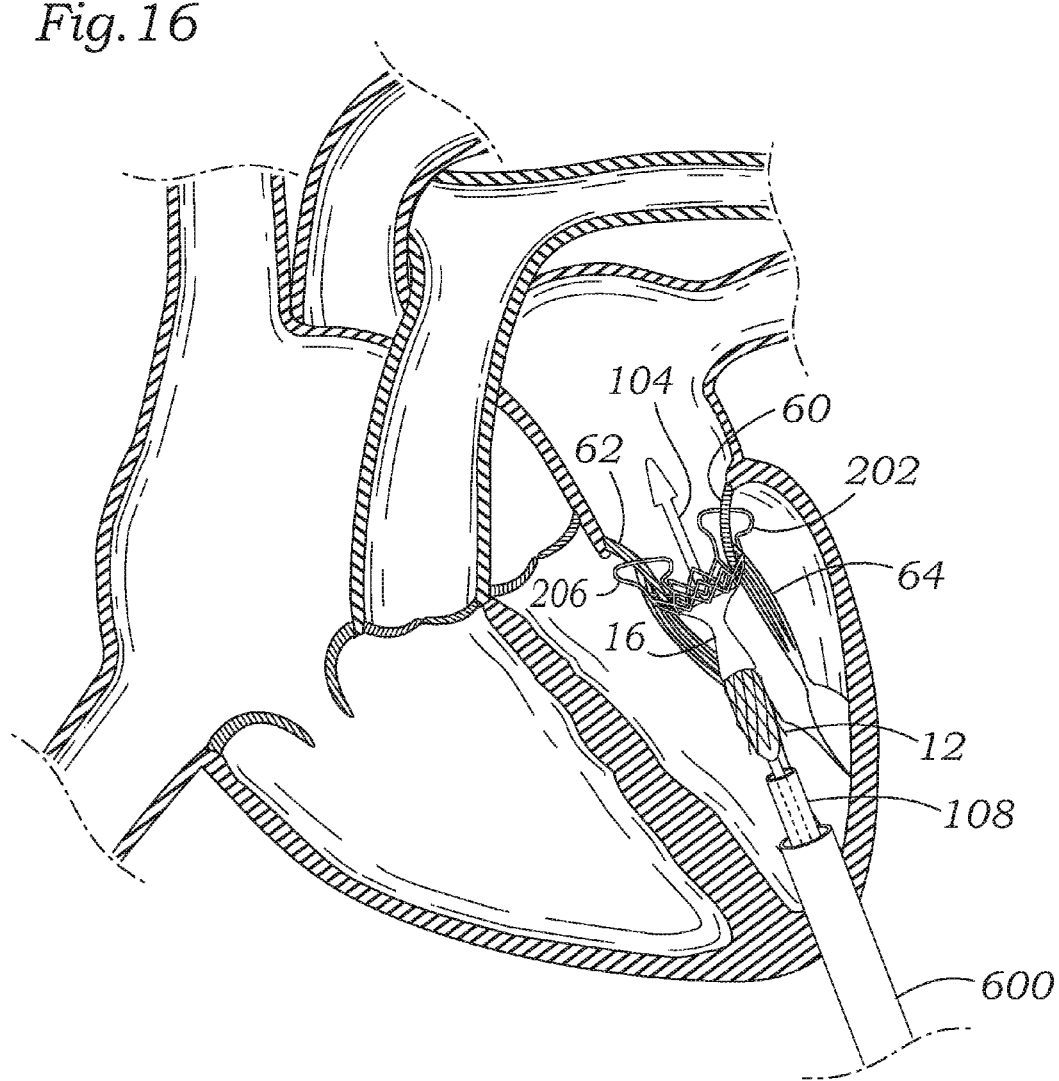
FIG. 16 shows an exemplary method for delivering and implanting the prosthetic valve assembly of FIGS. 7A-7C at the native mitral valve of the heart via a transventricular approach.

As noted above, any of the prosthetic valve assemblies disclosed herein can be delivered in a transventricular approach. FIG. 16, for example, shows the prosthetic valve assembly 200 of FIGS. 7A-7C being delivered in a transventricular approach. As shown, an introducer 600 can be inserted through an opening or puncture made in the chest and the left ventricle of the heart, such as at the bare sport on the lower anterior ventricle wall. The delivery apparatus 100 can be inserted through the introducer 600 to position the valve assembly 200 in the left ventricle. The sheath 108 can then be retracted to allow the outer anchor 202 to expand. The shaft 104 can be manipulated to place the fixation members 206 behind the native leaflets and/or native chordae tendineae by advancing the shaft 104 in the distal direction. Further advancement of the shaft 104 in the distal direction causes the sleeve 16 and the valve component 12 to be positioned within the native leaflets, as depicted in FIG. 8B. Thereafter, the valve component 12 can be expanded by inflating the balloon 106.

In alternative embodiments, the outer anchor of a prosthetic valve assembly (e.g., anchor 14) can have a D-shaped cross-section in a plane perpendicular to the longitudinal axis A of the anchor to better conform to the shape of the native mitral valve annulus.

In some embodiments, the outer anchor of a prosthetic valve assembly (e.g., anchor 14) can be deployed inside of the native leaflets 60, 62 rather than on the outside of the native leaflets. In such embodiments, the outer anchor can have barbs on the outside of the anchor that can engage or penetrate the native leaflets 60, 62 when the outer anchor is deployed.

In some embodiments, the sleeve 16 of a prosthetic valve assembly can comprise a swellable hydrophilic material that can swell upon contact with blood and create a tighter seal with the native leaflets and the valve component 12.

In some embodiments, the outer anchor of a prosthetic valve assembly (e.g., anchor 14) can have barbs or projections on the inner surface of the anchor. The barbs or projections can extend radially inwardly from the inner surface of the anchor and can engage the sleeve 16 or the valve component 12 directly and/or press the native leaflets inwardly against the sleeve 16 or the valve component to help anchor the valve component in place relative to the outer anchor.

In alternative embodiments, any of the prosthetic valve assemblies disclosed herein can include a valve component and an anchor without a flexible sleeve interconnecting the valve component and the anchor. In such embodiments, the valve component and the anchor can be delivered on the same delivery apparatus or on separate delivery apparatuses. For example, when two separate delivery apparatus are used, one delivery apparatus can be used to deliver one component of the valve assembly from one access location (e.g., through the wall of the left ventricle) while the other delivery apparatus can be used to deliver the other component of the valve assembly from another access location (e.g., through the wall of the left atrium or through the atrial septum). Delivery apparatuses that can be used to deliver a valve assembly having a valve component and an anchor that are not connected to each other during delivery are disclosed in U.S. Patent Publication No. US2012/0022633, which is incorporated herein by reference.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A method comprising:
    introducing a delivery apparatus into a patient's body, wherein a prosthetic valve assembly is mounted on a distal end portion of the delivery apparatus;
    advancing the prosthetic valve assembly into the left ventricle of the heart of the patient;
    radially expanding an anchor of the prosthetic valve assembly;
    positioning axially extending fixation members of the anchor behind the native mitral valve leaflets and/or the chordae tendineae; and
    radially expanding a valve component of the prosthetic valve assembly within the anchor, which causes the fixation members to pivot inwardly against the native mitral valve leaflets, thereby clamping the native mitral valve leaflets between the anchor and the valve component.

2. The method of claim 1, wherein the valve component and the anchor are axially spaced apart from each other on the delivery apparatus when the prosthetic valve assembly is introduced into the body and advanced into the left ventricle, and wherein after radially expanding the anchor but prior to radially expanding the valve component, the valve component is moved axially to a location within the anchor.

3. The method of claim 2, wherein the prosthetic valve assembly comprises a flexible sleeve having a first end portion secured to the valve component and a second end portion secured to the anchor.

4. The method of claim 3, wherein moving the valve component to a location within the anchor comprises retracting the delivery apparatus and the valve component proximally toward the left atrium while the anchor is engaged with the native mitral valve leaflets.

5. The method of claim 4, wherein the valve component is radially compressed on an inflatable balloon prior to being radially expanded and wherein radially expanding the valve component comprises inflating the balloon.

6. The method of claim 2, wherein radially expanding the anchor comprises deploying the anchor from a sheath, which causes the anchor to radially self-expand to an expanded state.

7. The method of claim 2, wherein the anchor has a tapered shape when radially expanded and becomes cylindrical when the valve component is expanded within the anchor.

8. The method of claim 2, further comprising, after radially expanding the anchor and positioning the fixation members behind the native mitral valve leaflets and/or the native chordae tendineae but prior to radially expanding the valve component, rotating the delivery apparatus relative to a longitudinal axis of the delivery apparatus to rotate the anchor, causing the fixation members to twist and pull the native mitral valve leaflets and/or the native chordae tendineae radially inwardly such that subsequent expansion of the valve component in the anchor clamps the native mitral valve leaflets and/or the native chordae tendineae in a twisted and pulled position between the anchor and the valve component.

9. The method of claim 1, wherein the fixation members define a first angle with respect to a central longitudinal axis of the anchor before the fixation members pivot inwardly and a second angle with respect to the axis after the fixation members pivot inwardly, wherein the first angle is larger than the second angle.

10. The method of claim 1, wherein the anchor comprises an annular base and each of the fixation members has a fixed end connected to the annular base and an opposing free end spaced axially from the annular base, the free ends of the fixation members defining an inflow end of the anchor, and wherein the act of expanding the valve component within the anchor comprises expanding the valve component within the annular base, causing the valve component to exert a radial outwardly directed force against the annular base, which causes the free ends of the fixation members to pivot inwardly.

11. A method comprising:
    introducing a delivery apparatus into a patient's body, wherein a prosthetic valve assembly is mounted on a distal end portion of the delivery apparatus, wherein the prosthetic valve assembly comprises an anchor having a plurality of cantilevered fixation members extending from an annular base of the anchor and a valve component axially separated from the anchor comprising a radially compressible and expandable frame and a valve structure supported inside the frame;
    radially expanding the anchor;
    positioning the fixation members behind the native mitral valve leaflets and/or the chordae tendineae of the patient;
    after positioning the fixation members behind the native mitral valve leaflets and/or the chordae tendineae of the patient, moving the valve component axially to a location within the anchor; and after moving the valve component axially to a location within the anchor, radially expanding the valve component, which causes the fixation members to pivot inwardly against the native mitral valve leaflets, thereby clamping the native mitral valve leaflets between the anchor and the valve component.

12. The method of claim 11, wherein radially expanding the valve component causes a radially outwardly directed force to be exerted against the base of the anchor, thereby causing the fixation members to pivot inwardly.

13. The method of claim 11, wherein the fixation members define a first angle with respect to a central longitudinal axis of the anchor before the fixation members pivot inwardly and a second angle with respect to the axis after the fixation members pivot inwardly, wherein the first angle is larger than the second angle.

14. The method of claim 11, wherein the anchor in the expanded state is tapered in a direction extending from the base of the anchor toward the fixation members, and wherein radially expanding the valve component causes the anchor to further expand to a cylindrical shape.

15. The method of claim 11, wherein the prosthetic valve assembly further comprises a flexible sleeve having a first end portion secured to the valve component and a second end portion secured to the anchor.

16. The method of claim 11, wherein the prosthetic valve assembly further comprises a flexible, invertible connector having a first surface, a second surface, a first end portion secured to the frame, and a second end portion secured to the anchor, and wherein moving the valve component axially to a location within the anchor causes the connector to move from a first configuration in which the first surface is an inner surface and the second surface is an outer surface to a second configuration in which the first surface is an outer surface and the second surface is an inner surface.

17. The method of claim 11, wherein radially expanding the valve component comprises radially expanding the valve component until the valve component bears against the annular base of the anchor, thereby causing the annular base to expand radially, which in turn causes the fixation members to pivot inwardly.

18. The method of claim 11, wherein the fixation members extend axially from the annular base and are circumferentially spaced apart from each other around the annular base.

19. The method of claim 18, wherein each fixation member has a fixed end connected to the annular base and an opposing free end spaced axially from the annular base.

20. A method comprising:
introducing a delivery apparatus into a patient's body, wherein a prosthetic valve assembly is mounted on a distal end portion of the delivery apparatus;
advancing the prosthetic valve assembly into the left ventricle of the heart of the patient;
radially expanding an anchor of the prosthetic valve assembly, the anchor comprising an annular base defining an outflow end of the anchor and a plurality of cantilevered fixation members extending axially from the annular base, each of the fixation members having a fixed end connected to the annular base and an opposing free end spaced axially from the annular base, the free ends of the fixation members defining an inflow end of the anchor;
positioning the fixation members of the anchor behind the native mitral valve leaflets and/or the chordae tendineae;
positioning a valve component of the prosthetic valve assembly within the annular base of the anchor; and
radially expanding the valve component within the annular base of the anchor, causing the valve component to exert a radial outwardly directed force against the annular base, which causes the free ends of the fixation members to pivot inwardly inwardly against the native mitral valve leaflets, thereby clamping the native mitral valve leaflets between the anchor and the valve component.

* * * * *